United States Patent [19]

Iwai

[11] Patent Number: 5,564,426
[45] Date of Patent: Oct. 15, 1996

[54] BLOOD PRESSURE MEASURING SYSTEM

[75] Inventor: Nobuo Iwai, Hikone, Japan

[73] Assignee: Matsushita Electric Works, Ltd., Osaka, Japan

[21] Appl. No.: 211,720

[22] PCT Filed: Aug. 23, 1993

[86] PCT No.: PCT/JP93/01176

§ 371 Date: Apr. 25, 1994

§ 102(e) Date: Apr. 25, 1994

[87] PCT Pub. No.: WO94/04074

PCT Pub. Date: Mar. 3, 1994

[30] Foreign Application Priority Data

Aug. 26, 1992 [JP] Japan ................................. 4-226616

[51] Int. Cl.⁶ .................................................. A61B 5/0225
[52] U.S. Cl. ................................... 128/680; 128/681
[58] Field of Search ................................... 128/672, 677, 128/680–3

[56] References Cited

U.S. PATENT DOCUMENTS

| | | | |
|---|---|---|---|
| 4,263,918 | 4/1981 | Swearingen et al. | 128/681 |
| 4,484,584 | 11/1984 | Uemura | 128/680 |
| 4,751,930 | 6/1988 | Terada . | |
| 4,860,760 | 8/1989 | Miyawaki et al. | 128/680 |
| 5,054,494 | 10/1991 | Lazzaro et al. | 128/677 |
| 5,099,853 | 3/1992 | Uemura et al. | 128/681 X |

FOREIGN PATENT DOCUMENTS

| | | |
|---|---|---|
| 63-238847 | 10/1988 | Japan . |
| 3-11219 | 2/1991 | Japan . |
| 3-92132 | 4/1991 | Japan . |

Primary Examiner—Angela D. Sykes
Attorney, Agent, or Firm—Nikaido, Marmelstein, Murray & Oram LLP

[57] ABSTRACT

By a pressure data separating device 24, a net cuff pressure and an arterial pulse component are separately extracted from a cuff pressure of an occluding cuff which is an electrical signal provided from an A/D converter 23. A waveform value indicative of a waveform of each arterial pulse is computed by an arterial pulse deriving section 24a. An arithmetic operation device 26 is capable of detecting a characteristic value from a time series of the waveform values and determining systolic and diastolic blood pressures of a subject in accordance with a net cuff pressure corresponding to the characteristic value. In the present invention, since particular times associated with the systolic and diastolic blood pressures are derived by an analysis of the waveform of each arterial pulse, the blood pressures can be accurately determined while preventing an error in measurement caused by individual difference of the subject.

21 Claims, 25 Drawing Sheets

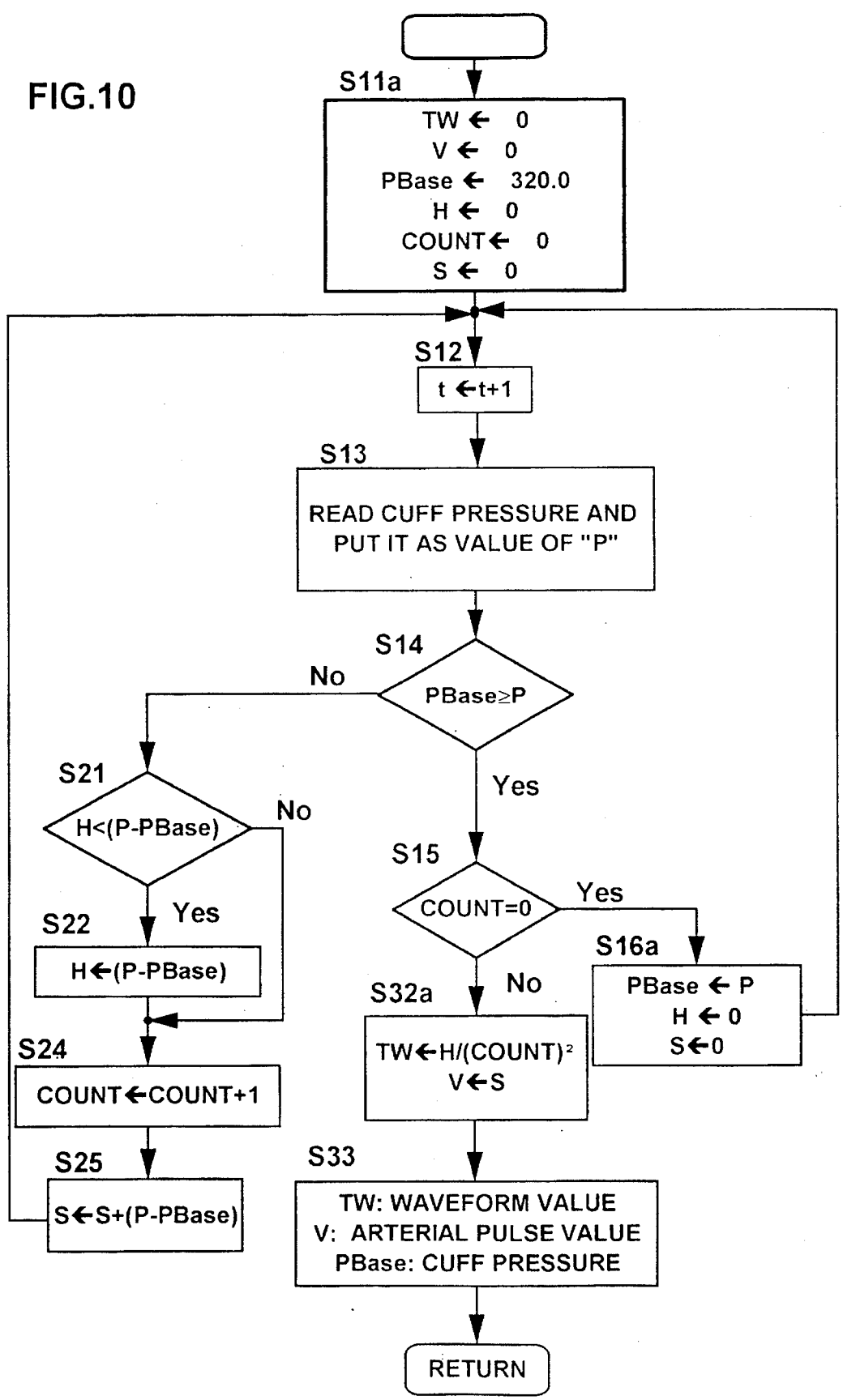

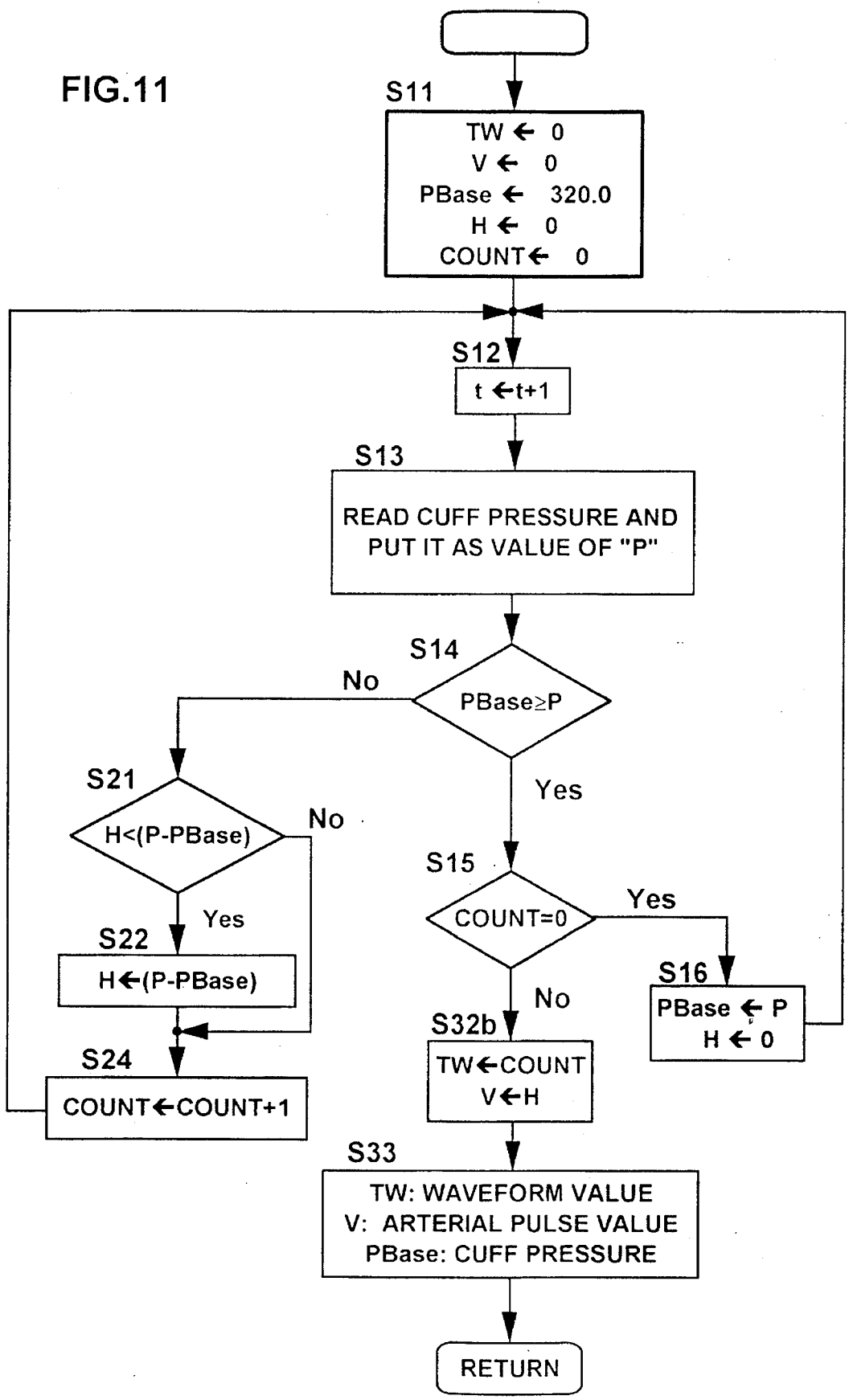

FIG. 18
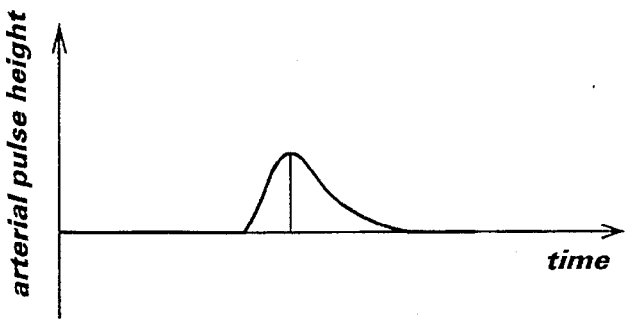
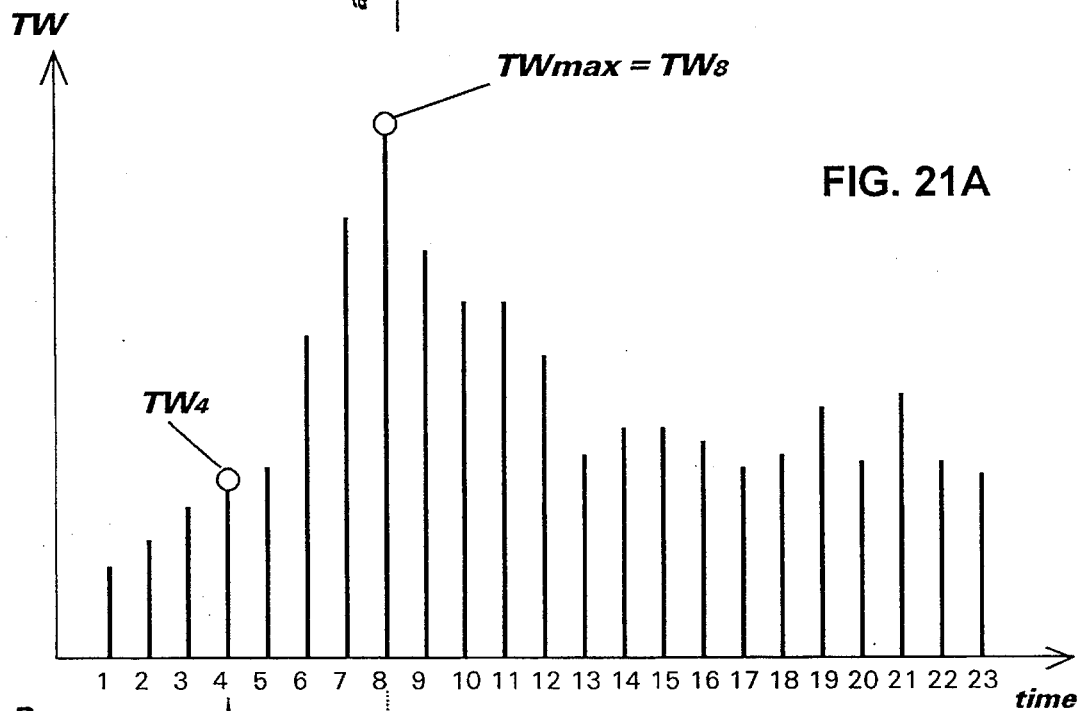
FIG. 21A
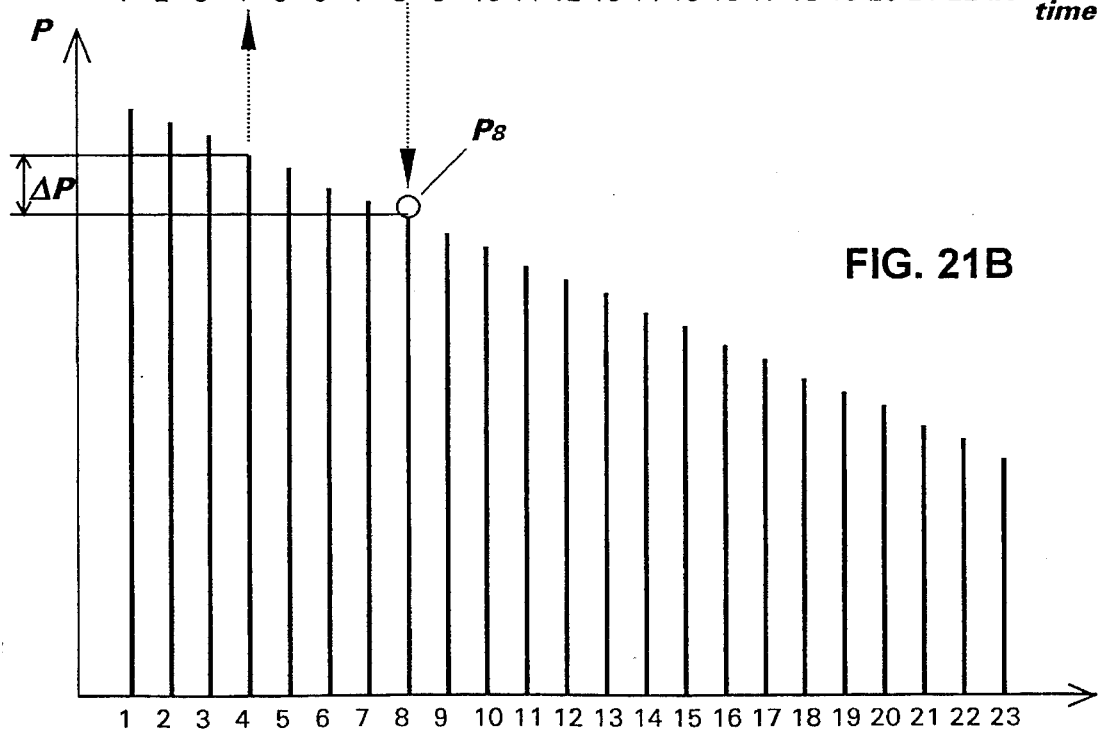
FIG. 21B

FIG.25A

| | DTW(0) | DTW(1) | DTW(2) | DTW(3) | DTW(4) |
|---|---|---|---|---|---|
| DPS(0) | DT(0,0,0) | DT(0,1,0) | DT(0,2,0) | DT(0,3,0) | DT(0,4,0) |
| DPS(1) | DT(0,0,1) | DT(0,1,1) | DT(0,2,1) | DT(0,3,1) | DT(0,4,1) |
| DPS(2) | DT(0,0,2) | DT(0,1,2) | DT(0,2,2) | DT(0,3,2) | DT(0,4,2) |
| DPS(3) | DT(0,0,3) | DT(0,1,3) | DT(0,2,3) | DT(0,3,3) | DT(0,4,3) |
| DPS(4) | DT(0,0,4) | DT(0,1,4) | DT(0,2,4) | DT(0,3,4) | DT(0,4,4) |

FIG.25B

|        | DTW(0)     | DTW(1)     | DTW(2)     | DTW(3)     | DTW(4)     |
|--------|------------|------------|------------|------------|------------|
| DPS(0) | DT(1,0,0)  | DT(1,1,0)  | DT(1,2,0)  | DT(1,3,0)  | DT(1,4,0)  |
| DPS(1) | DT(1,0,1)  | DT(1,1,1)  | DT(1,2,1)  | DT(1,3,1)  | DT(1,4,1)  |
| DPS(2) | DT(1,0,2)  | DT(1,1,2)  | DT(1,2,2)  | DT(1,3,2)  | DT(1,4,2)  |
| DPS(3) | DT(1,0,3)  | DT(1,1,3)  | DT(1,2,3)  | DT(1,3,3)  | DT(1,4,3)  |
| DPS(4) | DT(1,0,4)  | DT(1,1,4)  | DT(1,2,4)  | DT(1,3,4)  | DT(1,4,4)  |

BLOOD PRESSURE MEASURING SYSTEM

TECHNICAL FIELD

The present invention is related to a blood pressure measuring system utilizing an oscillometric method, which is characterized by extracting an arterial pulse component superimposed on a cuff pressure of each arterial pulse, and deriving particular times indicative of systolic and diastolic blood pressures in accordance with a variation of the arterial pulse component.

BACKGROUND ART

In the past, there has been known a blood pressure measuring system (Japanese Patent publication [KOKOKU] No. 3-11219) utilizing an oscillometric method, which is characterized by extracting an arterial pulse component superimposed on a cuff pressure of each arterial pulse, and deriving particular times indicative of systolic and diastolic blood pressures in accordance with a variation of the arterial pulse component. In the blood pressure measuring system, the arterial pulse component is defined as a pulse height of the arterial pulse.

By the way, since the pulse height of each arterial pulse is varied in response to a bloodstream of a selected portion of a subject to which an occluding cuff is attached, an extent of the variation is influenced by individual difference. In particular, when the variation of the pulse height is small at a particular time indicative of the systolic or diastolic blood pressure of the subject, it is difficult to accurately derive the systolic or diastolic blood pressure from the pulse height. Therefore, there is a probability of causing an error of measurement.

A primary object of the present invention is to provide a blood pressure measuring system capable of accurately determining systolic and diastolic blood pressures of a subject while preventing the occurrence of an error of measurement.

DISCLOSURE OF INVENTION

A blood pressure measuring system of the present invention comprises an occluding cuff adapted in use to be attached to a selected portion of a subject, a pressurizing device for providing an occluding pressure of the occluding cuff, a pressure bleeding device for gradually decreasing the occluding pressure, a pressure sensor, a pressure data separating device, a blood pressure determining device and a display. The pressure sensor is for sensing an instantaneous cuff pressure and providing an electrical signal indicative thereof. The pressure data separating device is for separating from the electrical signal an arterial pulse component superimposed on a net cuff pressure during a pressure bleeding period of gradually decreasing the occluding pressure so as to separately extract the net cuff pressure and the arterial pulse component. The blood pressure determining device is for determining systolic and diastolic blood pressures in accordance with the net cuff pressure and the arterial pulse component provided from the pressure data separating device. In particular, the pressure data separating device includes a waveform analyzing section for computing a waveform value indicative of a waveform of each arterial pulse. In addition, the blood pressure determining device includes a characteristic value detecting section for detecting a characteristic value from a time series of the waveform values and a blood pressure deriving section for deriving the systolic and diastolic blood pressures in accordance with the net cuff pressure corresponding to the characteristic value. Therefore, the blood pressure measuring system of the present invention is capable of computing the waveform value indicative of the waveform of each arterial pulse, detecting the characteristic value from the time series of the waveform values, and deriving the systolic and diastolic blood pressures in accordance with the net cuff pressure corresponding to the characteristic value. That is, particular times indicative of the systolic and diastolic blood pressures are derived in accordance with a variation of the waveform of the arterial pulse, so that an accurate measurement of the systolic and diastolic blood pressures can be performed while preventing an error of measurement caused by individual difference.

In a preferred embodiment of the present invention, the pressure data separating device includes an arterial pulse deriving section for providing, for each arterial pulse, an arterial pulse value which is a pulse height or pulse area of the arterial pulse. The pulse area is an integral of the arterial pulse with respect to time. In addition, the blood pressure determining device includes a first blood pressure deriving section for deriving first systolic and diastolic blood pressures based upon the waveform values, a second blood pressure deriving section for deriving second systolic and diastolic blood pressures based upon the arterial pulse values, and a blood pressure compensation section for determining the systolic and diastolic blood pressures in accordance with the first and second systolic and diastolic blood pressures. In this system, since the systolic blood pressure is determined in accordance with the first systolic blood pressure derived based upon the waveform values and the second systolic blood pressure derived based upon the arterial pulse values, it is possible to more accurately determine the systolic blood pressure of the subject as compared with the case of determining the systolic blood pressure in accordance with one of the first or second systolic blood pressures.

BRIEF DESCRIPTION OF THE DRAWINGS

FIG. 10 is a flow chart showing procedures of a second embodiment of the present invention;

FIG. 11 is a flow chart showing procedures of a third embodiment of the present invention;

FIG. 18 is a waveform diagram explaining an analysis of an arterial pulse of a tenth embodiment of the present invention;

FIGS. 21A and 21B are diagrams for explaining an analysis of arterial pulses of a thirteenth embodiment of the present invention;

FIGS. 25A and 25B are data tables used in a fourteenth embodiment of the present invention.

BEST MODE FOR CARRYING OUT THE INVENTION

The present invention is explained in detail referring to the attached drawings.

FIRST EMBODIMENT

Figure 1:
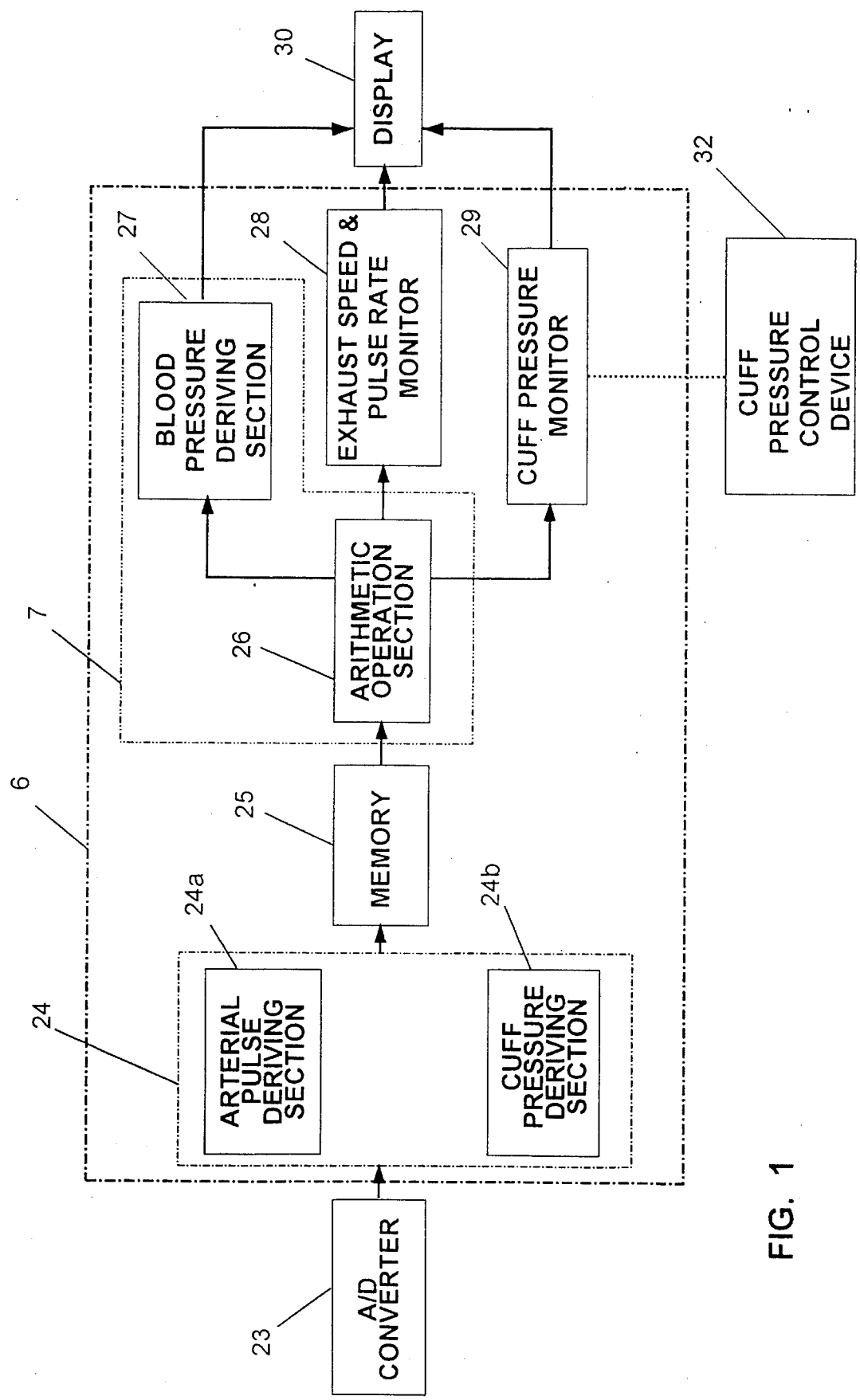
FIG. 1 is a block diagram showing a blood pressure measuring system of a first embodiment of the present invention.
Figure 2:
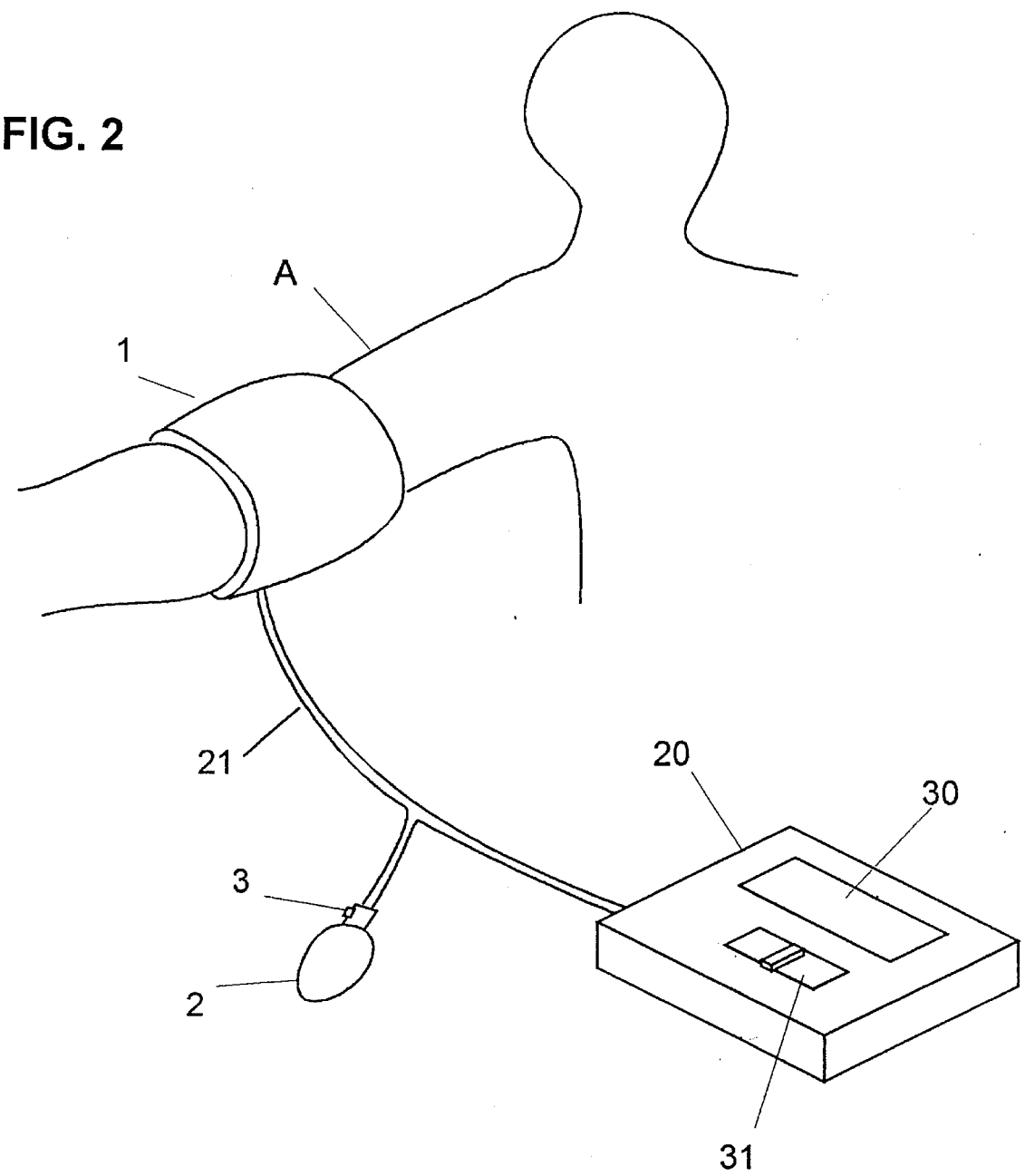
FIG. 2 is a schematic view of an apparatus embodying the blood pressure measuring system, the apparatus being shown with its occluding cuff fitted around the upper arm of a subject.

A basic constituent of a blood pressure measuring system is explained referring to FIGS. 1 to 4. As shown in FIG. 2, the system comprises an occluding cuff I adapted in use to be attached to a selected portion of a subject, for example, an upper arm A of the subject, an inflation bulb 2 as a pressurizing device which is connected with the occluding cuff through a rubber tube 21, and a pressure control valve 3 as a pressure bleeding device. The rubber tube 21 is also connected with an apparatus body 20 of the system to perform a blood pressure measurement of the subject in accordance with an internal pressure of the tube 21, which is equal to an internal pressure (cuff pressure) of the occluding cuff 1.

Figure 4:
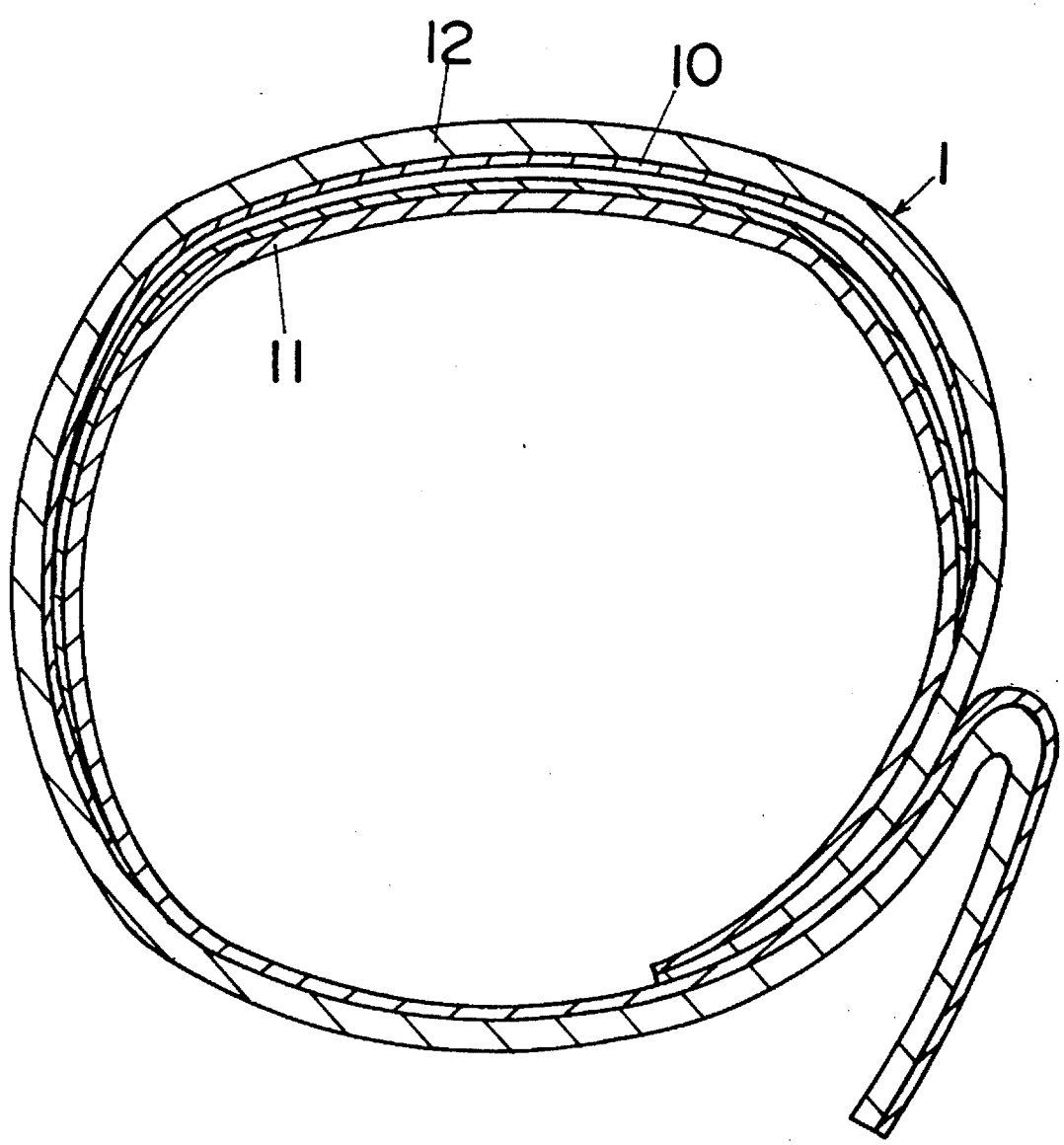
FIG. 4 is a cross-sectional view of the occluding cuff used in the first embodiment.

As shown in FIG. 4, the occluding cuff 1 comprises an inside cloth 11, an outside cloth 12, and a rubber bag 10 disposed therebetween. Since the rubber bag 10 is formed with a thin rubber sheet to improve a compliance thereof, it is possible to sensitively detecting an arterial pressure superimposed on a net cuff pressure. Therefore, it is preferred that the inside cloth 11 is made of a light and expandable material and the rubber bag 10 is made such that a required toughness of the rubber bag 10 can be maintained even if a step of inflating the rubber bag 10 more than 300 mmHg is repeated. In addition, for preventing an influence of the inside cloth 11 to the compliance of the rubber bag 10, it is possible to directly contact the rubber bag 10 with the subject's body without using the inside cloth 11. The apparatus body 20 and a portion of the rubber bag 10 are connected by the rubber tube 21 in order to transmit a variation of the cuff pressure to the apparatus body 20 through the tube 21. On the other hand, for sensitively transmitting the variation of the cuff pressure without damping it, it is preferred that the outside cloth 12 does not expand in spite of a winding diameter of the occluding cuff 1, a magnitude of the cuff pressure, and a deformation of the rubber bag 10 during an inflation step. Therefore, the outside cloth 12 should be made of a material having a relatively low compliance. A shape of the occluding cuff 1 is determined in accordance with Japanese Industrial Standard (JIS). In addition, as the winding diameter of the occluding cuff i is varied in response to the selected portion of the subject to which the occluding cuff 1 is attached, it is desired to use the occluding cuff 1 having a winding diameter adequate for the selected portion.

A pressurized air is supplied to the rubber bag 10 of the occluding cuff i through the rubber tube 21 by repeating a pump-up action of the inflation bulb 2, so that the inflated occluding cuff 1 pressurizes the selected portion of the subject. An occluding pressure of the cuff 1 is increased until a bloodstream of the selected portion is occluded. On the other hand, the pressure control valve 3 is for gradually decreasing the occluding pressure. That is, after stopping the pump-up action of the inflation bulb 2, the pressurized air of the occluding cuff 1 is gradually exhausted to the outside through the pressure control valve 3. During a pressure bleeding period of gradually decreasing the occluding pressure, particular times indicative of systolic and diastolic blood pressures are derived in accordance with the arterial pressure superimposed on the net cuff pressure, and then net cuff pressures corresponding to the particular times are determined as systolic and diastolic blood pressures of the subject, respectively.

A resonant frequency of a closed acoustic space, which is composed of the occluding cuff 1, the inflation bulb 2, the pressure control valve 3, the apparatus body 20 and the rubber tube 21, is set to be sufficiently higher than a frequency (2–10 Hz) of an arterial pulse. That is, even if the resonant frequency is varied by undesirable quality of parts of the system, it is set so as not to give a bad influence to the frequency zone of the arterial pulse. In addition, for transmitting the arterial pressure to the apparatus body 20 through the rubber tube 21 without damping it, it is preferred that a length of the rubber tube 21 is set about 50 cm, and the rubber tube 21 is made of a relatively hard material in order to prevent a deformation thereof caused by the arterial pressure.

Figure 3:
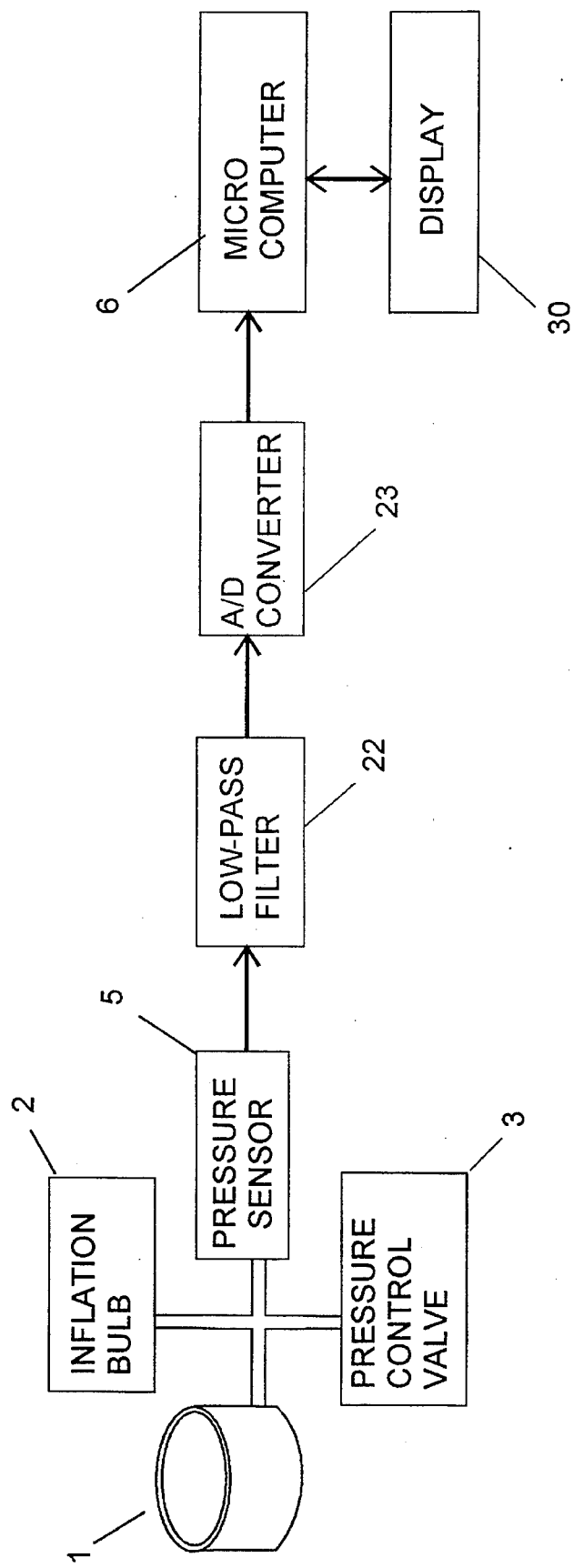
FIG. 3 is a block diagram of the above system.

AS shown in FIG. 3, the apparatus body 20 comprises a pressure sensor 5 for sensing an instantaneous cuff pressure transmitted through the rubber tube 21 and providing an electrical signal indicative of the arterial pressure and the net cuff pressure. The instantaneous cuff pressure is detected with a built-in diaphragm of the pressure sensor. The diaphragm should be selected from the viewpoints of response and frequency properties to sensitively detect the arterial pressure. Noise signals included in an output of the pressure sensor 5 are removed by a low-pass filter 22 having a cut-off frequency of about 10 to 20 Hz. The low-pass filter 22 is capable of removing noise signals occurring from the inside of the subject's body, the occluding cuff 1, and the circumference, and passing only signal corresponding to the arterial pressure superimposed on the net cuff pressure. The signal from the low-pass filter 22 is sampled at a constant sampling cycle by an A/D (Analog/Digital) converter 23, in which each of sampled values is converted to the corresponding digital value. The sampling cycle is sufficiently shorter than one cycle of the arterial pulse (For example, 10 to 100 sampling per second). A converting speed (Sample·Hold Time) of the A/D converter 23 is set in the range of one half to three fourth of the sampling cycle. When a slower converting speed is selected from the range, it is possible to smooth low-level noise signals which can not be removed by the low-pass filter 22.

AS shown in FIG. 1, a digital value as an output of the A/D converter 23 is sent to a pressure data separating device 24. The separating device 24 comprises an arterial pulse deriving section 24a and a cuff pressure deriving section 24b. By the separating device, an arterial pulse component (arterial pressure) superimposed on the net cuff pressure is separated from the net cuff pressure, so that the arterial pulse deriving section 24a outputs the arterial pulse component, and the cuff pressure deriving section 24b outputs the net cuff pressure. The arterial pulse component and the net cuff pressure provided form the separating device 24 are stored in a memory 25, and used for a comparative operation performed in an arithmetic operation section 26, as described later. The systolic and diastolic blood pressures of the subject are determined by a blood pressure deriving section 27 in accordance with results of the comparative operation. Thus determined systolic and diastolic blood pressures are displayed on a display 30. Therefore, a blood pressure determining device 7 comprises the arithmetic operation section 26 and the blood pressure deriving section 27. An exhaust speed of the pressurized air of the cuff 1 and a pulse rate of the subject are determined by an exhaust speed & pulse rate monitor 28 in accordance with the results of the arithmetic operation section 26, and displayed on the display 30. The cuff pressure of the occluding cuff 1 is measured by a cuff pressure monitor 29 and displayed on the display 30.

Operation switches 31, for example, for starting the blood pressure measurement, are arranged at the front face of the apparatus body 20 together with the display 30. The pressure data separating device 24, the memory 25, the arithmetic operation section 26, the blood pressure deriving section 27, the exhaust speed pulse rate monitor 28 and the cuff pressure monitor 29 are composed of a microcomputer 6 comprising a central processor unit (CPU), a program memory (ROM) and a data memory (RAM), etc., which is operated in accordance with a predetermined program. In the above embodiment, the inflation bulb 2 and the pressure control valve 3 are used as the pressurizing device and the pressure bleeding device, respectively. However, it is possible to use a pump and an electromagnetic valve as the pressurizing device and the pressure bleeding device. That is, as indicated by a dotted line of FIG. 1, it is preferred that the pump and the electromagnetic valve are controlled by a cuff pressure control device 32 in accordance with the cuff pressure provided from the cuff pressure monitor 29.

Figure 5:
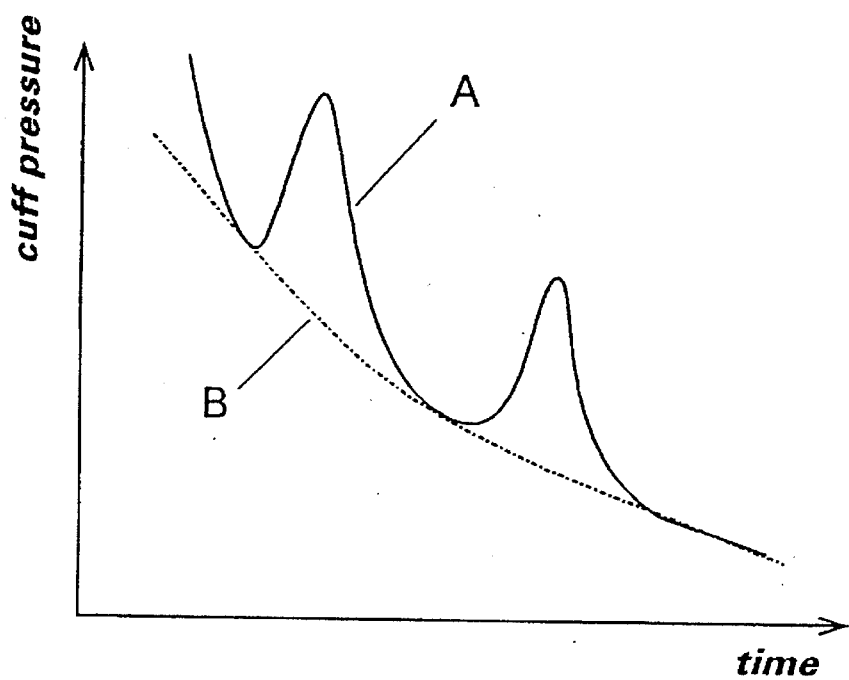
FIG. 5 is a waveform diagram showing an output of an A/D converter of the first embodiment.

Next, a method of determining a systolic blood pressure is explained. In this embodiment, the occluding cuff 1 is attached to the upper arm A of the subject. A pressurized air is supplied to the occluding cuff 1 by repeating the pump-up action of the inflation bulb 2 to occlude a bloodstream of the upper arm A. After stopping the pump-up action of the inflation bulb 2, the pressurized air of the occluding cuff 1 is gradually exhausted to the outside through the pressure control valve 3. During this exhausting period, an arterial pressure superimposed on a net cuff pressure is detected by the pressure sensor 5. After noise signals included in an analog signal of the pressure sensor 5 are removed by the low-pass filter 22, the analog signal passing through the low-pass filter 22 is converted to a digital signal by the A/D converter 23. The digital signal is input to the microcomputer 6. Analyzing procedures by the microcomputer 6 are explained below. The arterial pressure superimposed on the net cuff pressure is divided to the arterial pressure and the net cuff pressure by the pressure data separating device 24. That is, since an output of the A/D converter 23 corresponds to the arterial pressure superimposed on the net cuff pressure, when the output of the A/D converter 23 is varied, as indicated by the curve A drawn by a solid line of FIG. 5, the net cuff pressure is indicated by the curve B of FIG. 5 which is a downside envelop of the curve A. Therefore, a difference between the curves A and B is equal to the arterial pressure. By the way, in this method, it is not necessary for determining a value of the arterial pressure. It is enough to detect a variation of the arterial pressure. Therefore, The arterial pulse component (arterial pressure) is extracted by the arterial pulse deriving section 24a with the use of the curve A without determining the difference between the curves A and B. In the arterial pulse deriving section 24a, a waveform value TW of each arterial pulse is determined by performing a digital operation with respect to the curve A. In addition, the net cuff pressure corresponding to the curve B which is the downside envelope of the curve A is determined by the cuff pressure deriving section 24b.

Figure 7:
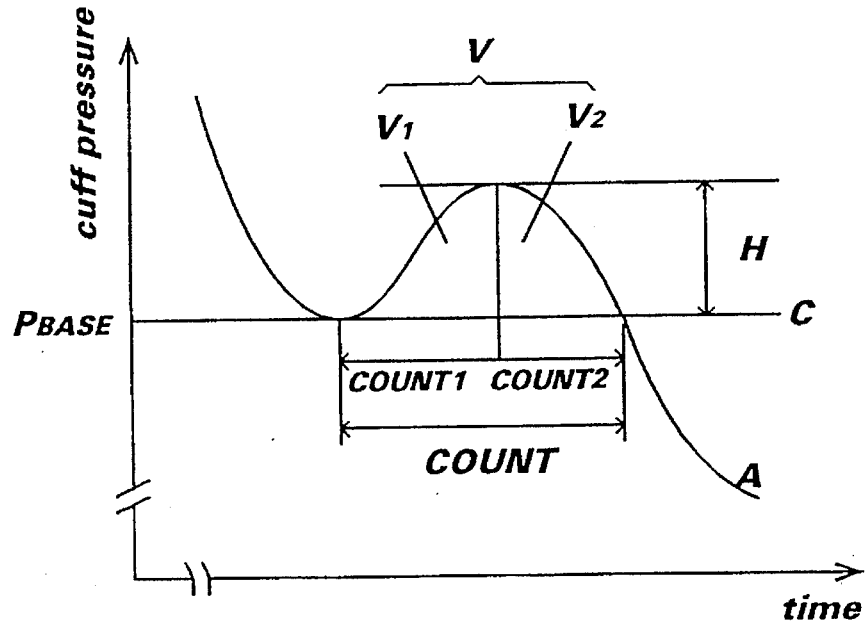
FIG. 7 Is a waveform diagram for explaining technical terms used in embodiments of the present invention.

As shown in FIG. 7, the waveform value TW is determined by the arterial pulse deriving section 24a. The waveform value TW is obtained by dividing a pulse height H by a pulse width COUNT with respect to a waveform of each arterial pulse, that is, by the following expression (1), $$TW = H/COUNT \tag{1}$$

wherein H is the pulse height which is defined as a difference between a line C passing through a minimum value PBase of a waveform corresponding to one of the arterial pulses of the curve A and a peak value of the waveform, and COUNT is the pulse width which is defined as a time period between two particular times indicating that a difference between the curve A and the line C is zero.

Figure 6:
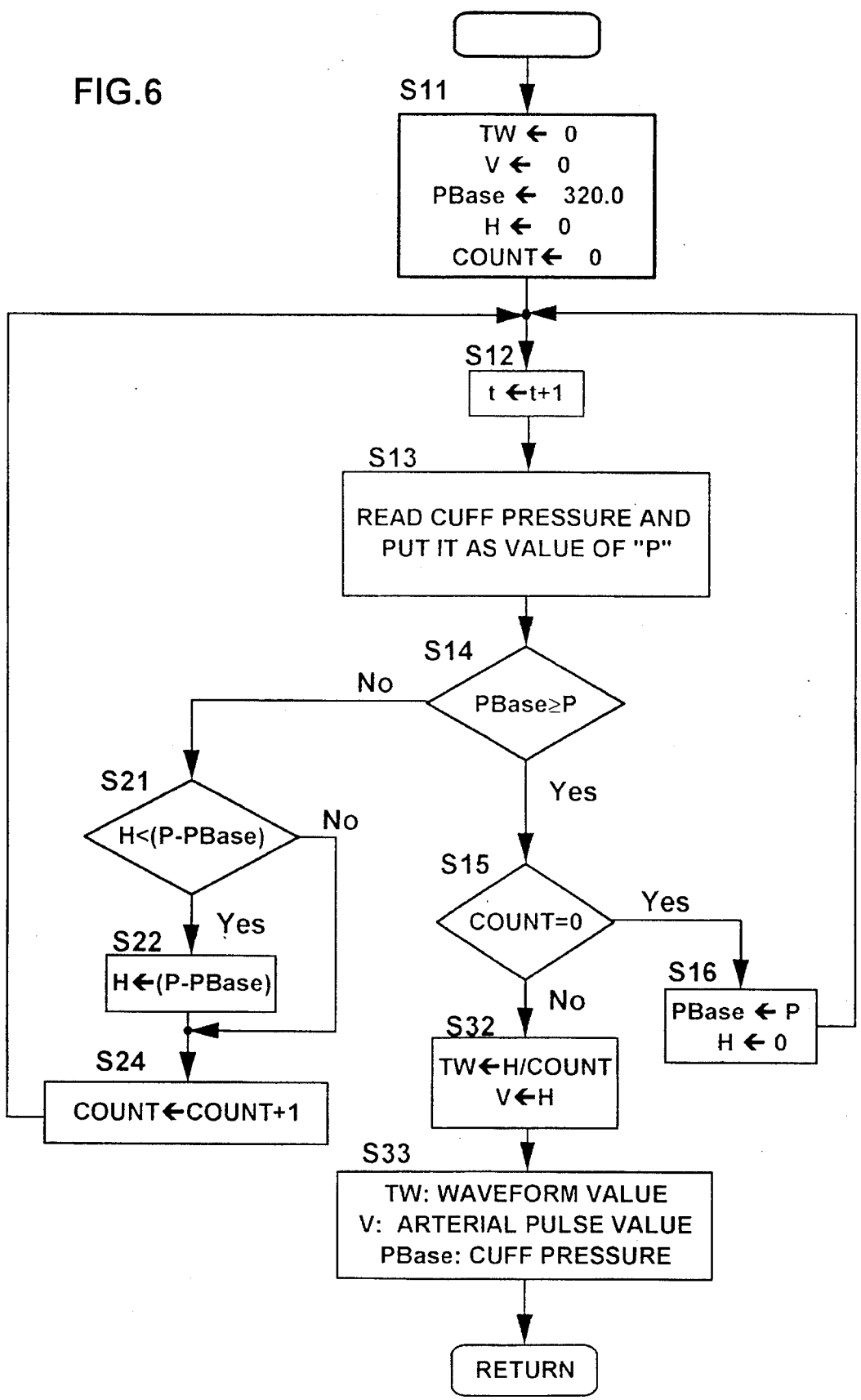
FIG. 6 is a flow chart showing procedures of the first embodiment of the present invention.

Concretely, the waveform value TW is determined in accordance with the following procedures, as shown in FIG. 6. First, initial values of the waveform value TW, an arterial pulse value V, the pulse height H and the pulse width COUNT are set zero at an initial stage (S11). An initial value of the minimum value PBase is set, for example, 320.0 mmHg, which is sufficiently higher than a practical systolic blood pressure. Subsequently, a sampled pressure is continuously read out at a sampling cycle (S12) and is put as an instantaneous cuff pressure P (S13). The cuff pressure P is compared with the minimum value PBase (S14). When the cuff pressure P is smaller than the minimum value PBase, that is, in case of a decrease tendency of the cuff pressure P, and also the pulse width COUNT is zero (S15), the cuff pressure P is set as a new minimum value PBase (S16). At the same time, the pulse height H is set zero. Continuously, next sampled pressure is read out (S12). By this loop (S14→S15→S16→S12→S13→S14), an analysis with respect to a region which is not surrounded with the curve A and the line C of FIG. 7 is performed.

On the other hand, when the cuff pressure P is larger than the minimum value PBase, that is, in case of an increase tendency of the cuff pressure P (S14), a difference between the cuff pressure P and the minimum value PBase is compared with the pulse height H (S21). When the pulse height H is smaller than the difference, that is, when the curve A is in an increase tendency in the region surrounded with the line C and the curve A of FIG. 7, the difference is set as a new pulse height H(S22). When the pulse height is larger than the difference between the cuff pressure P and the minimum value PBase, the pulse height H is not renewed. As explained above, after performing the comparison with respect to the pulse height H, "1" is added to the pulse width COUNT (S24). Continuously, next sampled cuff pressure is read out (S12). Since the minimum value PBase is not varied in this loop, the above procedures of this loop are repeated while PBase≧P is not satisfied. Therefore, an analysis with respect to the region surrounded with the line C and the curve A of FIG. 7 is performed by this loop, so that the difference between the peak value of the waveform of the curve A and the line C is finally determined as the pulse height H of the waveform, and also the time period between the two particular times indicating that the difference between the line C and the curve A is zero is determined as the pulse width COUNT.

When a next sampled pressure is smaller than the minimum value PBase, the procedure from the step S14 to the step S15 is carried out without repeating the above loop (S14→S21→(S22)→S24→S12→S13→S14). In this time, since the pulse width COUNT is not zero, the procedure from the step S15 to the step S32 is carried out. In the step S32, the waveform value TW is determined by the expression (1), and the pulse height H is used as the arterial pulse value V. The above explained procedures are performed with respect to each arterial pulse of the curve A, so that the waveform value TW and arterial pulse value V corresponding to the arterial pulse are determined (S33), and also the minimum value PBase is determined as a net cuff pressure at a particular time indicating the occurrence of the arterial pulse (S33).

A waveform analyzing section operates along a program containing the above explained procedures. Required data, which is selected from the waveform value TW, the arterial pulse value V and the minimum value PBase, is stored in the memory 25. As the data is obtained per arterial pulse, it is stored as a time series of the data in the memory 25.

Figure 8:
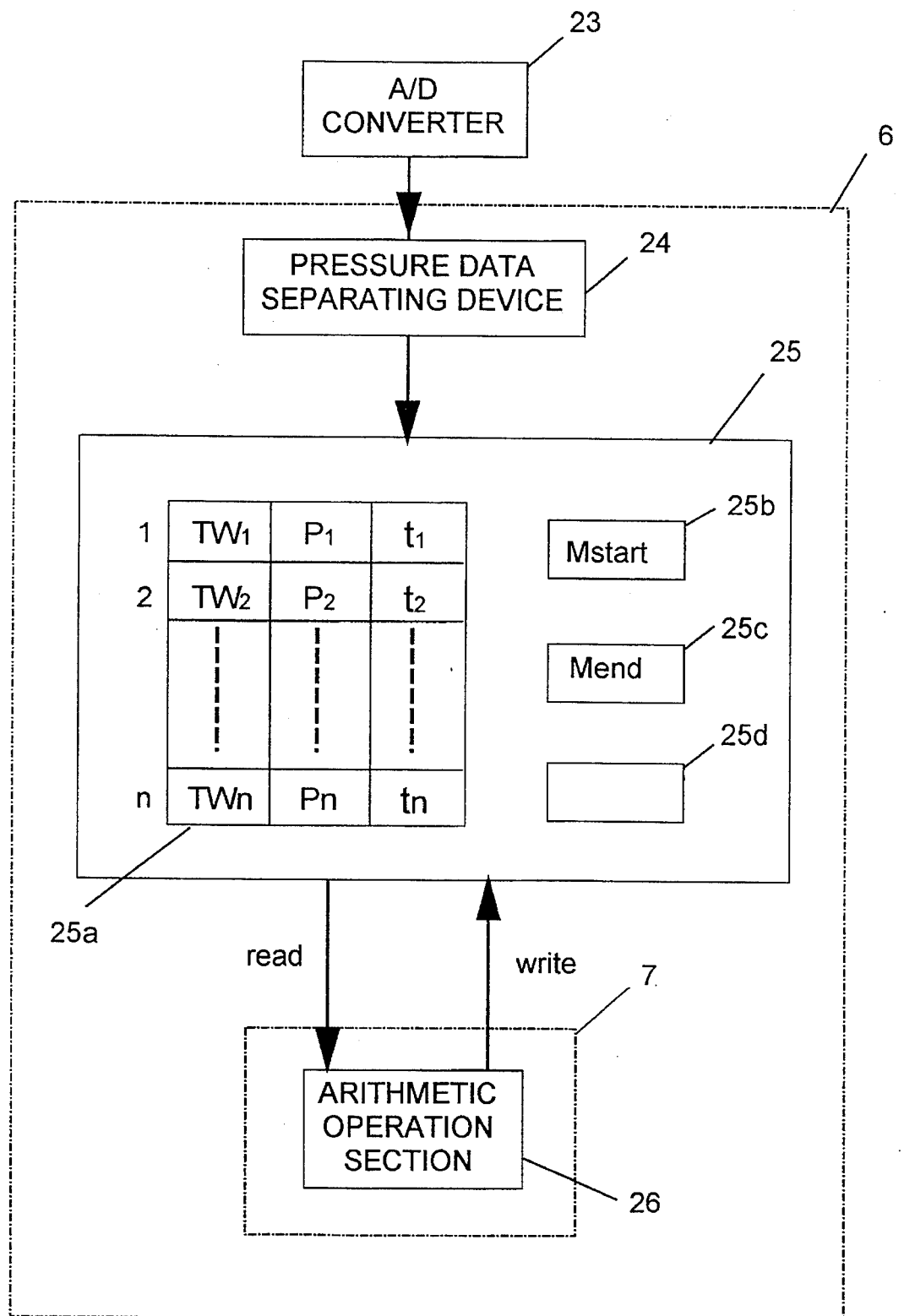
FIG. 8 is a block diagram showing an important portion of the blood pressure measuring system of the first embodiment.

After the time series of the data stored in the memory 25 is read out by the blood pressure determining device 7 comprising the arithmetic operation section 26 and the blood pressure deriving section 27, the following operations with respect to the time series are performed to determine systolic blood pressure of the subject. For example, a time series of the waveform values TW is designated as $TW_1, TW_2, \ldots$, a time series of the arterial pulse values V is designated as $V_1, V_2, \ldots$, a time series of the minimum values PBase is designated as net cuff pressures $P_1, P_2, \ldots$ Since a fixed sampling cycle is used, each of sampling times $t_1, t_2, \ldots$, is merely utilized as a guide number. In the blood pressure determining device 7 of this embodiment, the waveform values $TW_1, TW_2, \ldots$ and the net cuff pressures $P_1, P_2, \ldots$ are used as the required data. As shown in FIG. 8, for example, a set of the waveform value $TW_1$, the net cuff pressure $P_1$ and the sampling time $t_1$ is stored in a data storing range 25a of the memory 25. In addition, the memory 25 comprises a start point storing range 25b for storing a start point Mstart indicative of the address of a first data of the data storing range 25a, an end point storing range 25c for storing an end point Mend indicative of the address of a final data of the data storing range 25a, and a memory range 25d for storing another information.

Figure 9A:
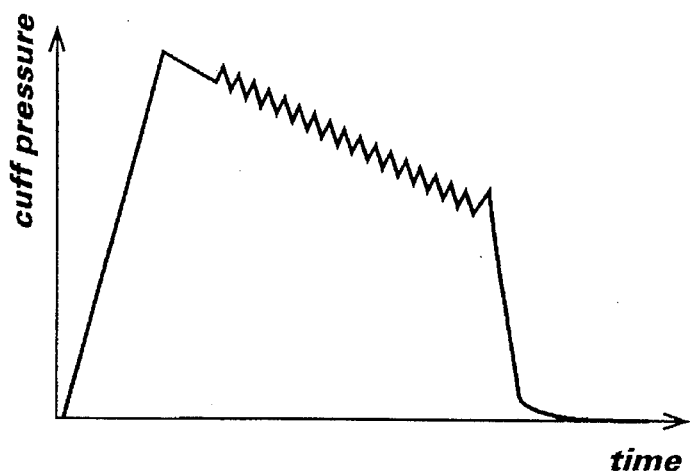
FIGS. 9A to 9C are diagrams for explaining an analysis of arterial pulses of the first embodiment.
Figure 9B:
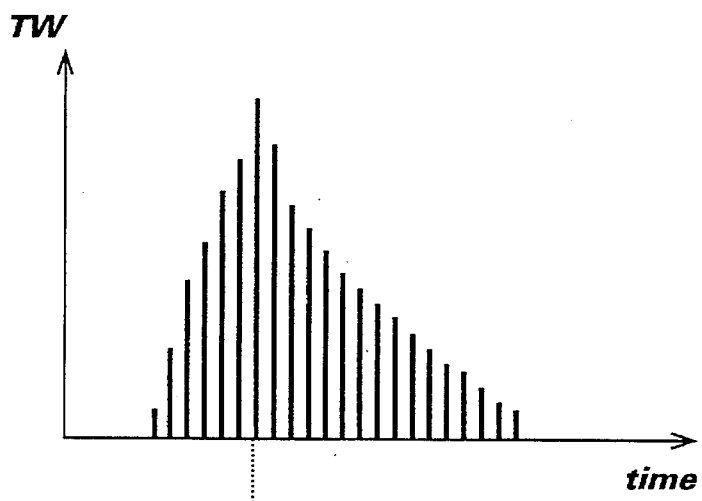
Figure 9C:
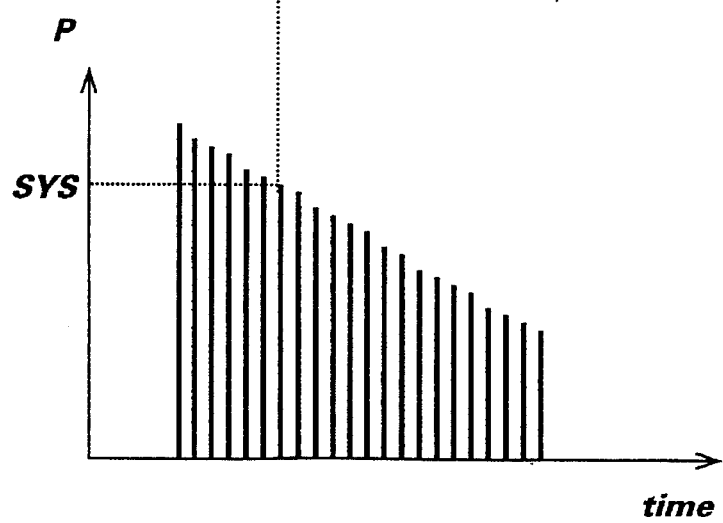

When an output of the A/D converter 23 is given by the diagram shown in FIG. 9A, a time series of the waveform values $TW_1, TW_2, \ldots$, is for example, shown in FIG. 9B and a time series of the net cuff pressures $P_1, P_2, \ldots$ is, for example, shown in FIG. 9C. In the arithmetic operation section 26, each of the waveform values $TW_1, TW_2, \ldots$ is, compared with a waveform value of the previous arterial pulse to determine a maximum waveform value. In the blood pressure deriving section 27, a particular net cuff pressure corresponding to the maximum waveform value is determined as the systolic blood pressure (SYS) of the subject. That is, the maximum waveform value, which is a boundary value between an increase tendency and a decrease tendency of the waveform values $TW_1, TW_2, \ldots$, is designated as a characteristic value. The net cuff pressure corresponding to the characteristic value is determined as the systolic blood pressure (SYS) of the subject.

By the way, when waveform values $TW_1, TW_2, \ldots$ having a different definition from the above case are used, it is also possible to determine a diastolic blood pressure of the subject in accordance with the above common procedures performed for determining the systolic blood pressure. In this embodiment, each of the waveform values $TW_1, TW_2, \ldots$ is obtained by dividing the arterial pulse value V by the pulse width COUNT. However, in place of the waveform value, it is possible to use a waveform value having a different definition, which is obtained by dividing the pulse width COUNT by the arterial pulse value V, that is, COUNT/V. In this case, a particular net cuff pressure corresponding to a minimum waveform value of the waveform values $TW_1, TW_2, \ldots$ is determined as the systolic blood pressure.

Thus determined the systolic and diastolic blood pressures are displayed on the display 30.

SECOND EMBODIMENT

In this embodiment, a waveform value TW is determined with respect to a waveform of each arterial pulse by dividing a maximum vale of a pulse height H OF the region surrounded with the line C and curve A of FIG. 7 by the square of a pulse width COUNT thereof. An arterial pulse value V is defined as an area S of the above described region. Concretely, the waveform value TW is determined in accordance with procedures of FIG. 10. That is, initial values of the waveform value TW, the arterial pulse value V, the pulse height H, the area S and the pulse width COUNT are set zero at an initial stage (S11a). An initial value of a minimum value PBase is set to 320.0 mmHg. Steps S12 to S15 are the same as the steps of the first embodiment, as shown in FIG.6. On steps S14 and S15, when a sampled cuff pressure P is smaller than the minimum value PBase, and the pulse width COUNT is zero, the cuff pressure P is set as a new minimum value PBase by a step S16a. At the same time, the pulse height H and the area S are set zero. On the other hand, on the step S14, when the cuff pressure P is larger than the minimum value PBase, a maximum difference between the cuff pressure P and the minimum value PBase is finally determined as the pulse height H of the region surrounded with the curve A and the line C in accordance with the same manner as the first embodiment (S21, S22). At the same time, a time period between two particular times indicating that a difference between the line C and the curve A is zero is determined as the pulse width COUNT. In addition, the area S of the region surrounded with the curve A and the line C is determined by integrating a difference between the cuff pressure P and the minimum value PBase (S25) with respect to time.

As described above, the waveform value TW is determined by dividing the pulse height H by the square of the pulse width COUNT. The area S is used as the arterial pulse value V (S32a). Required data, which is selected from the waveform TW, the arterial pulse value V and the minimum value PBase as a net cuff pressure, is stored in the memory 25. Of course, as the waveform value TW, it is also possible to use a reciprocal value of the above determined waveform value, which is obtained by dividing the square of the pulse width COUNT by the pulse height H. Procedures performed in this embodiment except for the above description are the substantially same as the first embodiment.

THIRD EMBODIMENT

In this embodiment, a waveform value TW is given as a pulse width COUNT, which is defined as a time period between two particular times indicating that a difference between the curve A and the line C of FIG. 7 is zero. That is, as shown in FIG. 11, the step S32 of the procedures shown in FIG. 6 of the first embodiment is replaced with a step S32b. Procedures performed in this embodiment except for the above description are the substantially same as the first embodiment.

FOURTH EMBODIMENT

In this embodiment, a waveform value TW is defined as a post-peak duration COUNT2 within a pulse width COUNT. The pulse width COUNT is defined as a time period between two particular times indicating that a difference between the curve A and the line C of FIG. 7 is zero. The pulse width COUNT is divided to a pre-peak duration COUNT1 and the post-peak duration COUNT2 by a specific time corresponding to a maximum value of a pulse height H of a waveform of the curve A of FIG. 7. The post-peak duration COUNT2 is defined as a time period after the specific time and within the pulse width COUNT. On the other hand, an arterial pulse value V is provided with an area S of a region surrounded with the curve A and the line C which is obtained in accordance with the same manner as the second embodiment.

Figure 12:
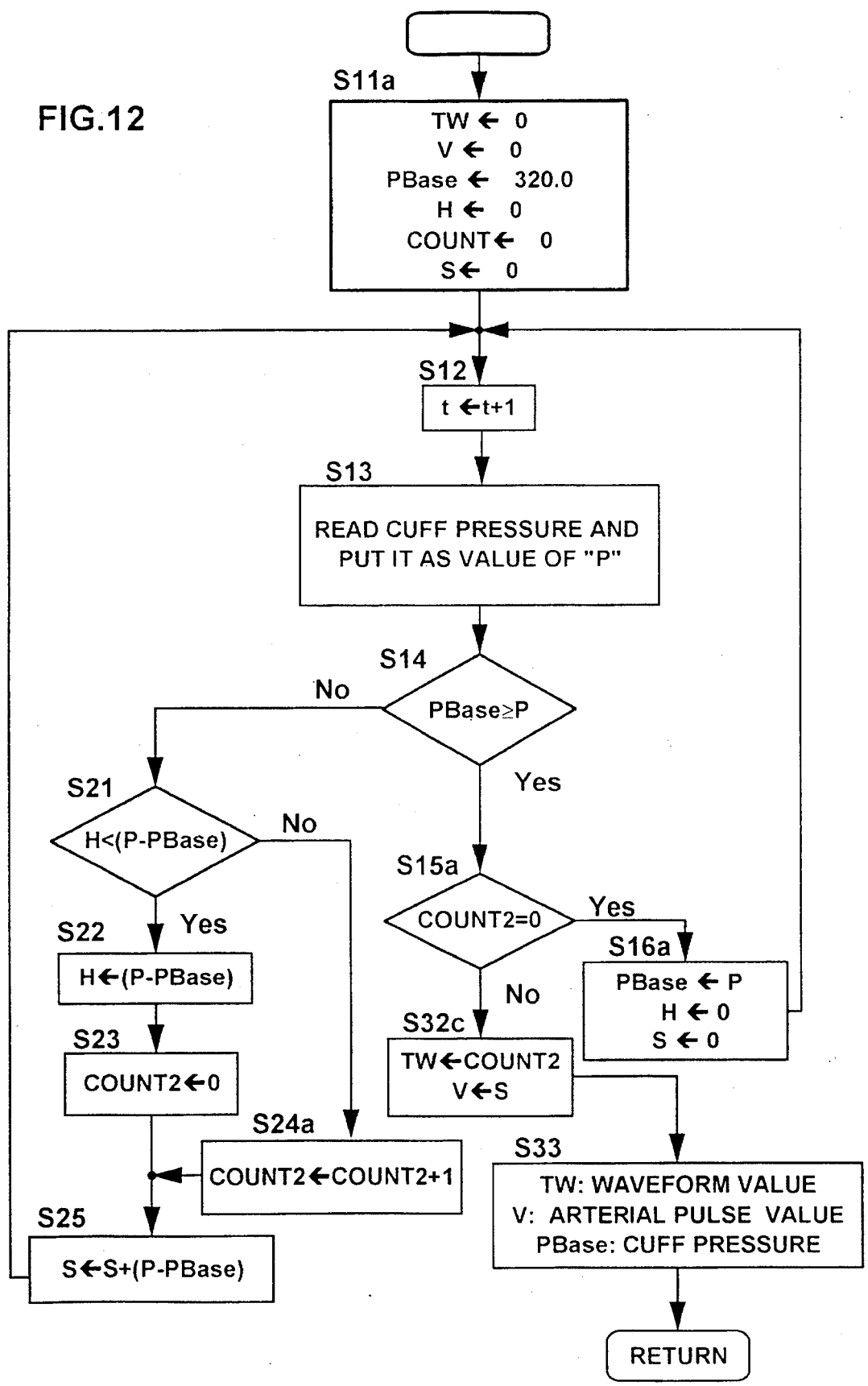
FIG. 12 is a flow chart showing procedures of a fourth embodiment of the present invention.

Procedures of determining the waveform value TW are shown in FIG. 12. That is, when a sampled cuff pressure P is smaller than a minimum value PBase, steps S11a to S16a which are the same procedures as the second embodiment are performed. On the other hand, when the sampled cuff pressure P is larger than the minimum value PBase, a difference between the cuff pressure P and the minimum value PBase is compared with the pulse height H (S21). When the difference is larger than the pulse height H, the difference is set as a new pulse height H and also the post-peak duration COUNT2 is set zero. When the difference is smaller than the pulse height H, "1" is added to the post-peak duration COUNT2 (S24a). An area S of the region surrounded with the curve A and the line C of FIG. 7 is also determined in accordance with the same manner as the second embodiment (S25).

By repeating the above procedures while PBase≧P is not satisfied, the post-peak duration COUNT2 and the area S are determined. In a step S32c, the post-peak duration COUNT2 and the area S are used as the waveform value TW and the arterial pulse value V, respectively. By the way, it is also possible to use the pre-peak duration COUNT1 as the waveform value TW. The pre-peak duration COUNT1 is defined as a time period before the specific time and within the pulse width COUNT. Procedures performed in this embodiment except for the above description are the substantially same as the first embodiment.

FIFTH EMBODIMENT

In this embodiment, a waveform value TW is given as a ratio of a pre-peak duration COUNT1 to a post-peak duration COUNT2 (=COUNT1/COUNT2). A pulse width COUNT is defined as a time period between two particular times indicating that a difference between the curve A and the line C of FIG. 7 is zero. The pulse width COUNT is divided to the pre-peak duration COUNT1 and the post-peak duration COUNT2 by a specific time corresponding to a maximum value of a pulse height H of a waveform of the curve A of FIG. 7. The pre-peak duration COUNT1 is defined as a time period before the specific time and within the pulse width COUNT. On the 10 other hand, an arterial pulse value V is given as an area S of a region surrounded with the curve A and the line C of FIG. 7.

Figure 13:
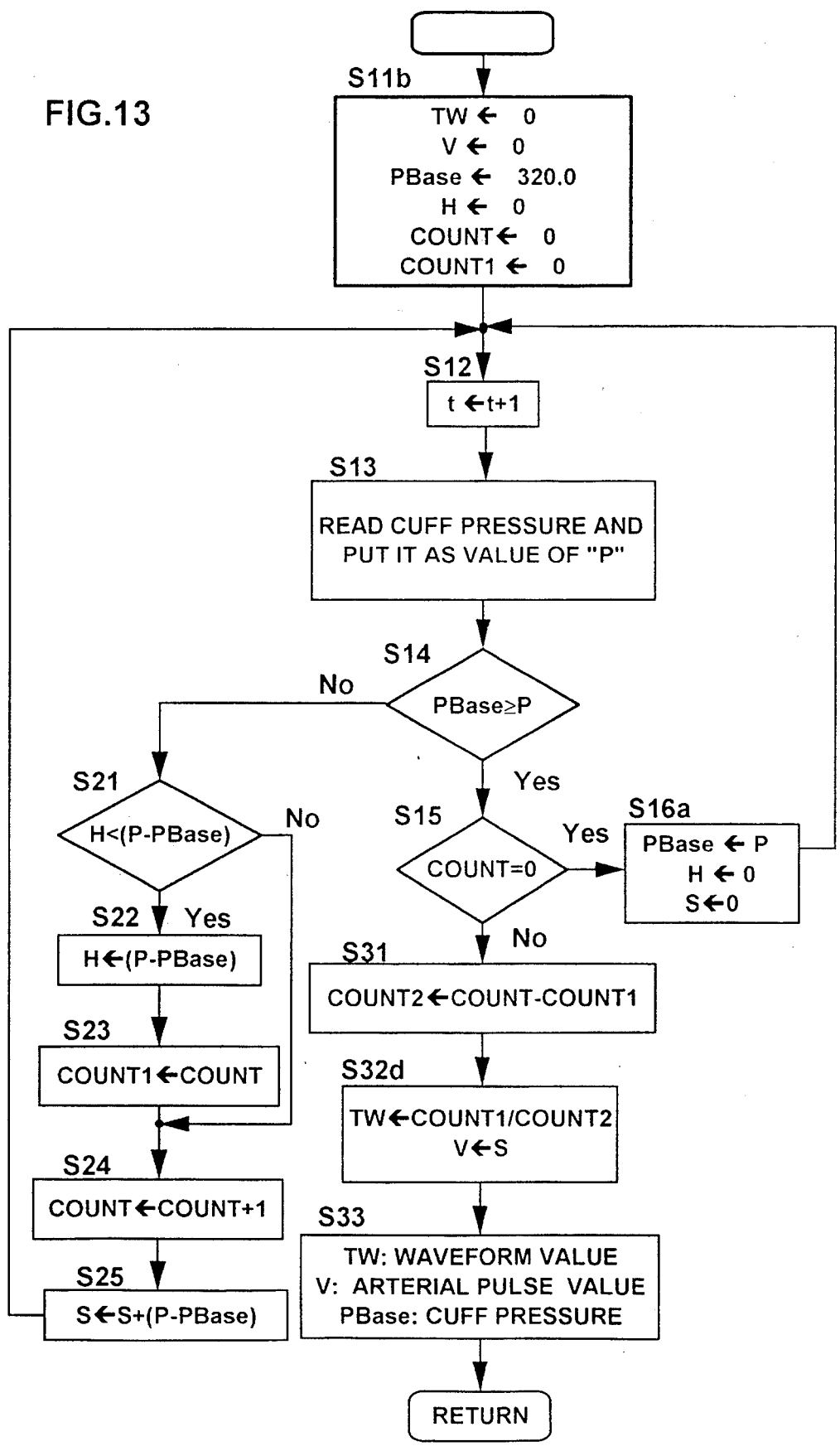
FIG. 13 is a flow chart showing procedures of a fifth embodiment of the present invention.

That is, procedures of determining the waveform value TW are shown in FIG. 13. In an initial step S11b, a pre-peak duration COUNT1 is set zero in addition to the initial values set in the second embodiment. Steps S12 to S16a, S21, S22, S24 and S25 are the same procedures as the second embodiment. In steps of determining the maximum value of the pulse height H of the region surrounded with the curve A and the line C, when a difference between a sampled cuff pressure P and a minimum value PBase is larger than the pulse height H, the difference is set as a new pulse height H (S22). The renewal of the pulse height H is continued while H<(P-PBase) is satisfied. At the same time, the pre-peak duration COUNT1 is determined (S23). After the maximum value of the wave height H, the pulse width COUNT, and the pre-peak duration COUNT1 are determined, the post-peak duration COUNT2 is obtained by subtracting the pre-peak duration COUNT1 from the pulse width COUNT (S31). Subsequently, the waveform value TW is determined by dividing the pre-peak duration COUNT1 by the post-peak duration COUNT2, and the area S of the region surrounded with the curve A and the line C is used as the arterial pulse value V (S32d). Of course, it is possible to use a ratio of the post-peak duration COUNT2 to the pre-peak duration COUNT1 (=COUNT2/COUNT1) as the waveform value TW. Procedures performed in this embodiment except for the above description are the substantially same as the first embodiment.

SIXTH EMBODIMENT

Figure 14:
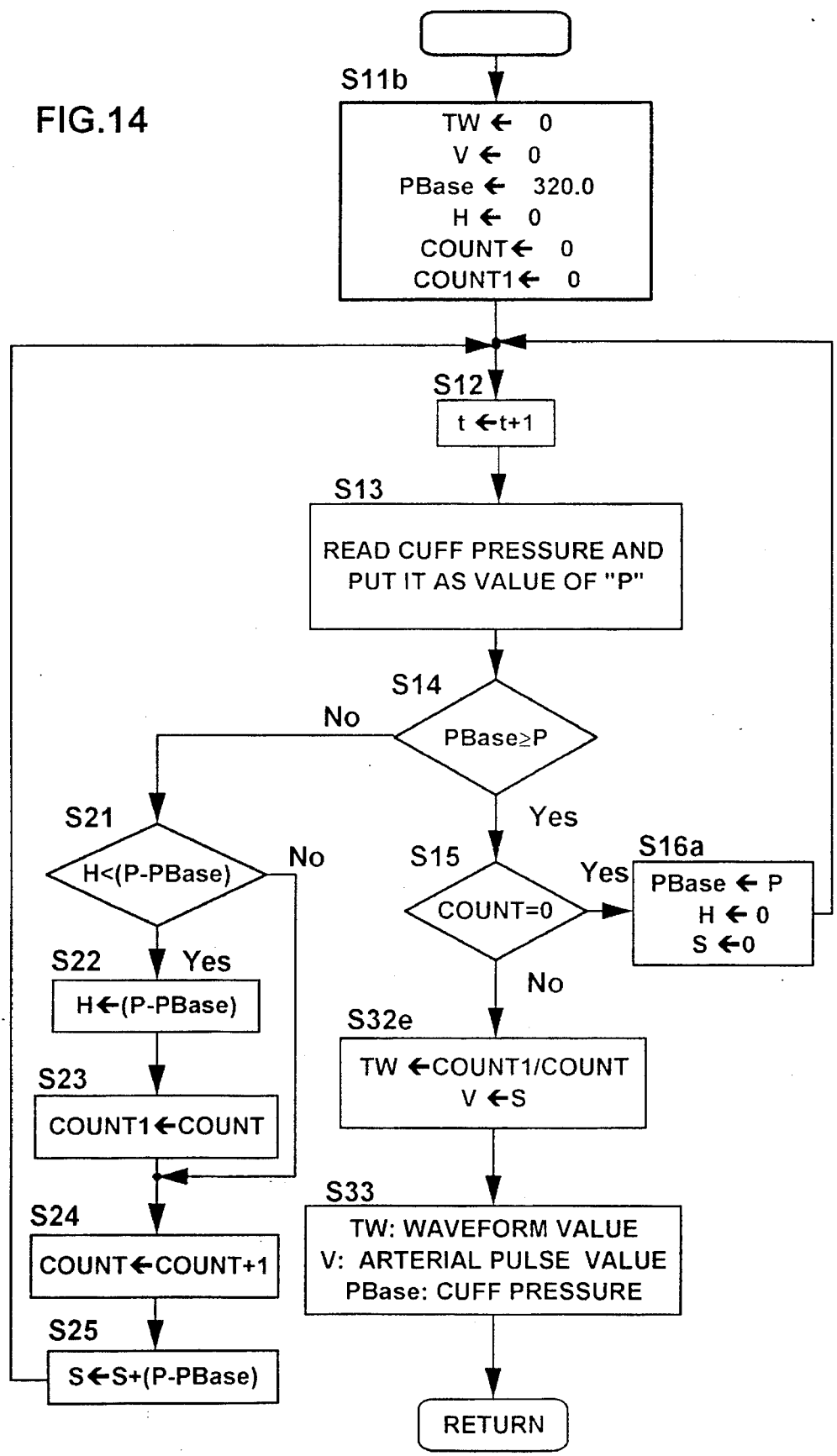
FIG. 14 is a flow chart showing procedures of a sixth embodiment of the present invention.

In this embodiment, as shown in FIG. 14, a waveform value TW is determined by dividing a pre-peak duration COUNT1 by a pulse width COUNT without calculating a post-peak duration COUNT2 (S32e). The pulse width COUNT is defined as a time period between two particular times indicating that a difference between the curve A and the line C of FIG. 7 is zero. The pulse width COUNT is divided to the pre-peak duration COUNT1 and the post-peak duration COUNT2 by a specific time corresponding to a maximum value of a pulse height H of a waveform of the curve A of FIG. 7. The pre-peak duration COUNT1 is defined as a time period before the specific time and within the pulse width COUNT.

Therefore, in this embodiment, a subtraction step S31 of the Fifth Embodiment is not required. Procedures performed in this embodiment except for the above description are the substantially same as the first embodiment. By the way, as the waveform value TW, it is possible to use a value obtained by dividing the pulse width COUNT by the pre-peak duration COUNT1. In addition, it is possible to use the post-peak duration COUNT2 in place of the pre-peak duration COUNT1 of this embodiment.

SEVENTH EMBODIMENT

In this embodiment, an area S of a region surrounded with the curve A and the line C of FIG. 7 is given as an arterial pulse value V. A rear-area S2 of the area S is used as a waveform value TW. The area S is divided to a fore-area S1 and the rear-area S2 which are integrals of the curve A of FIG. 7 respectively for a pre-peak duration COUNT1 and a post-peak duration COUNT2. The pre-peak and post-peak durations are defined in accordance with the same manner as the fourth embodiment.

Figure 15:
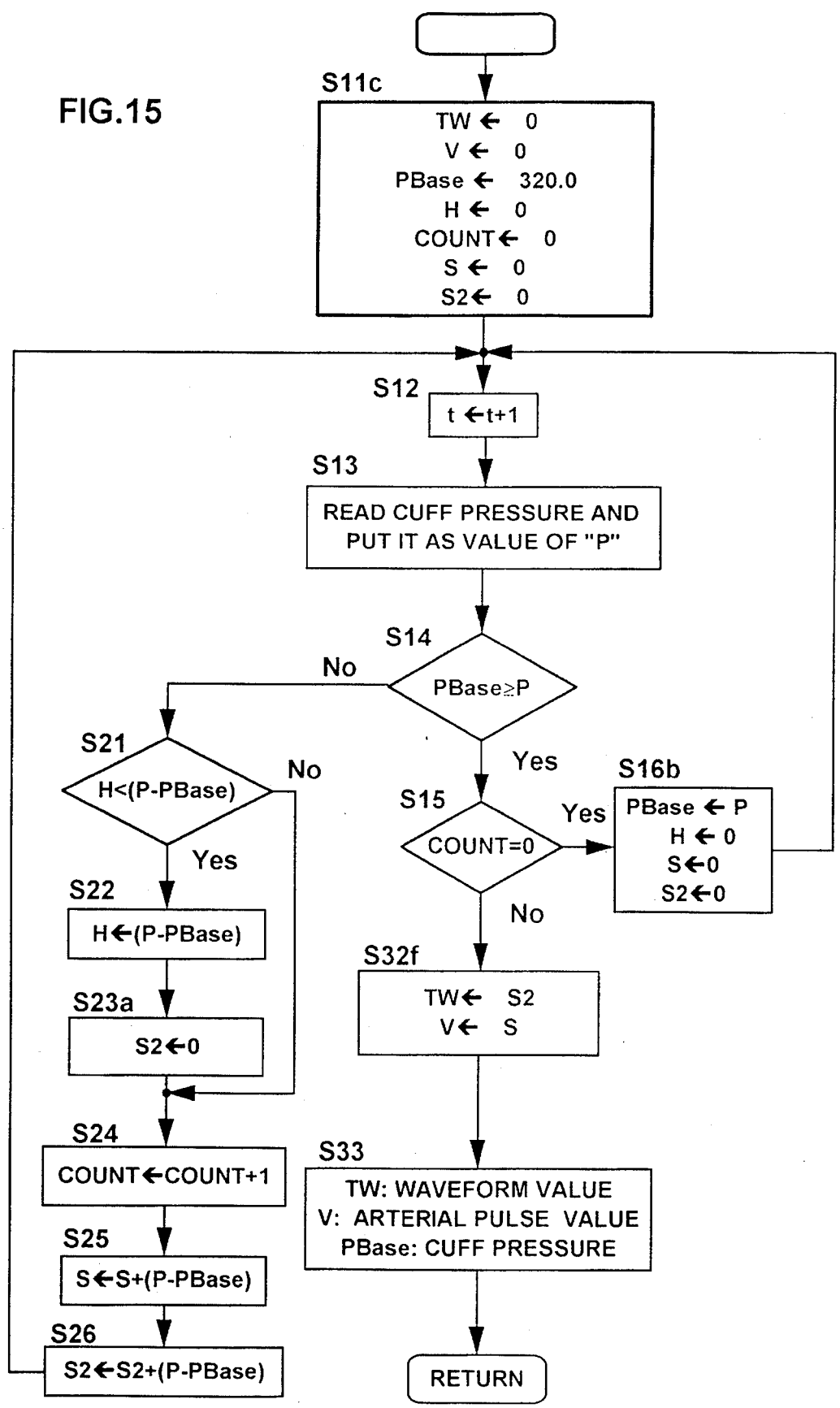
FIG. 15 is a flow chart showing procedures of a seventh embodiment of the present invention.

Procedures of determining the waveform value TW and the arterial pulse value V are shown in FIG. 15. Basically, the procedures is the same as the procedures explained in the second embodiment and shown in FIG. 10. That is, in an initial step S11c, the rear-area S2 is set zero in addition to the initial values set in the second embodiment. Steps S12 to S15 are the same procedures as the second embodiment. When a sampled cuff pressure P is smaller than a minimum value PBase, the pressure P is renewed as a new minimum value PBase. In this time, a pulse height H, the area S and the rear-area S2 are respectively set zero (S16b).

On the other hand, when the sampled cuff pressure P is larger than the minimum pressure PBase, the wave height H is determined by steps S21 and S22, and a pulse width COUNT and the area S is also determined by steps S24 and S25 in accordance with the same manner as the second embodiment. In addition, when a difference between the cuff pressure P and the minimum value PBase is larger than the pulse height H, that is, when the difference is in an increase tendency, the rear-area S2 is set zero (S23a). On the other hand, when the difference is smaller than the pulse height H, that is, when the difference is in a decrease tendency, the rear-area S2 is calculated by a step S26. Therefore, thus calculated rear-area S2 is used as the waveform value TW (S32f). Procedures performed in this embodiment except for the above description are the substantially same as the first embodiment. By the way, it is possible to use the fore-area S1 as the waveform value TW in place of the rear-area

EIGHTH EMBODIMENT

In this embodiment, a ratio of fore-area S1 to a rear-area S2 (=S1/S2) is used as a waveform value TW. An area S (=S1+S2) of a region surrounded with the curve A and the line C of FIG. 7 is given as an arterial pulse value V. The area S is divided to the fore-area S1 and the rear-area S2 which are integrals of the curve A of FIG. 7 respectively for a pre-peak duration COUNT1 and a post-peak duration COUNT2. The pre-peak and post-peak durations are defined in accordance with the same manner as the fourth embodiment.

Figure 16:
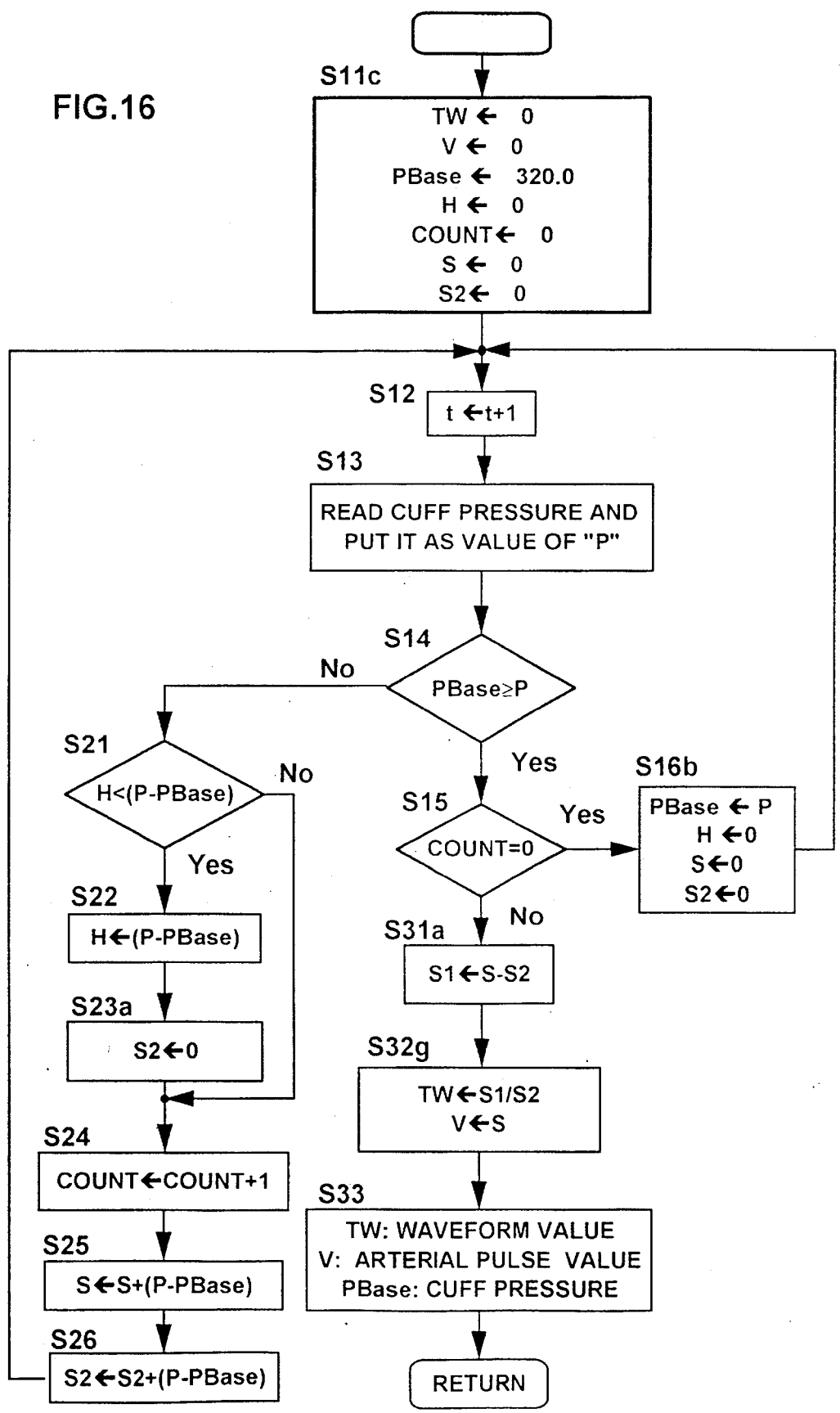
FIG. 16 is a flow chart showing procedures of an eighth embodiment of the present invention.

Procedures of determining the waveform value TW and the arterial pulse value V are shown in FIG. 16. By steps S11c to S16b and S21 to S26 of this embodiment which are the same as the steps of the seventh embodiment, the area S and rear-area S2 are determined. The fore-area S1 is determined by subtracting the rear-area S2 from the area S (S31a). Subsequently, the ratio of the fore-area S1 to the rear-area S2 and the area S are respectively used as the waveform value TW and the arterial pulse value V (S32g). Procedures performed in this embodiment except for the above description are the substantially same as the seventh embodiment. By the way, it is also possible to use a ratio of the rear-area S2 to the fore-area S1 (=S2/S1) as the waveform value TW.

NINTH EMBODIMENT

Figure 17:
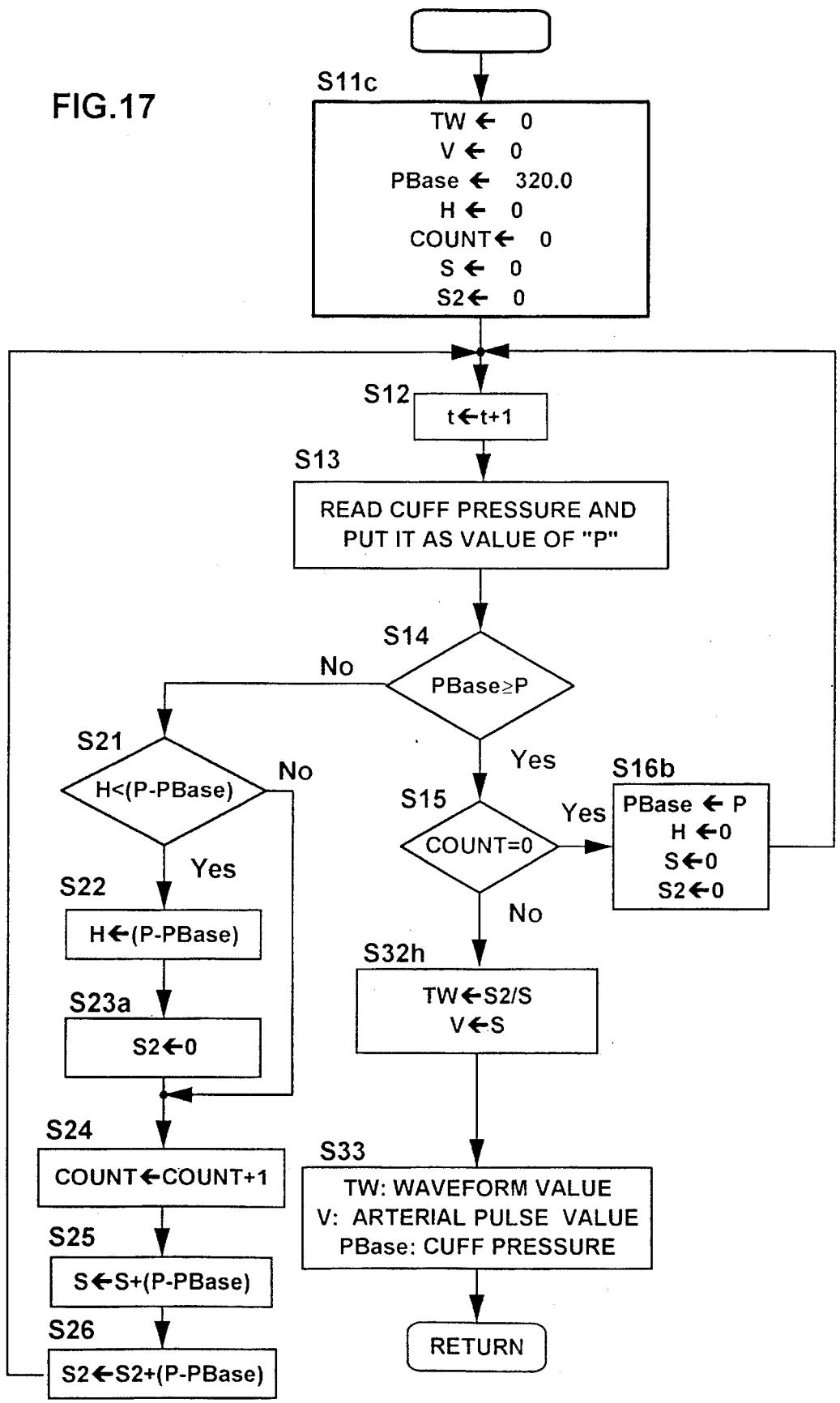
FIG. 17 is a flow chart showing procedures of a ninth embodiment of the present invention.

This embodiment is the substantially same as the eighth embodiment except that a ratio of the rear-area S2 to the area S is used as the waveform value TW. That is, as shown in FIG. 17, the substraction step S31a of the eighth embodiment is not required in this embodiment. By the way, it is possible to use a ratio of the area S to the rear-area S2, or a ratio of the fore-area S1 to the area S as the waveform value TW.

TENTH EMBODIMENT

In the above explained embodiments, a minimum value PBase is used as a base line of a waveform of an arterial pulse. However, in this embodiment, pressures corresponding to start and end points of the arterial pulse are set zero by subtracting the curve B from the curve A of FIG. 7, as shown in FIG. 18. Therefore, a waveform value TW and an arterial pulse value V are determined by applying the procedures of the first or ninth embodiment to the waveform of FIG. 18. The subtraction step is readily performed by the use of a digital filter after the A/D (analog/digital) converter 23, or the use of a bypass filter before the A/D converter 23. Procedures performed in this embodiment except for a method of separating an arterial pressure from a net cuff pressure are the substantially same as the above embodiments.

ELEVENTH EMBODIMENT

In the above embodiments, a net cuff pressure corresponding to a maximum waveform value detected form a time series of waveform values $TW_1, TW_2, \ldots$ is determined as a systolic blood pressure by the blood pressure determining device 7. However, in this embodiment, a difference between each of the waveform values $TW_1, TW_2, \ldots$ and a waveform value of the previous arterial pulse is detected to determine a maximum difference therebetween. A waveform value TW corresponding to the maximum difference is defined as a characteristic value. Finally, one of the net cuff pressures $P_1, P_2, \ldots$ corresponding to the characteristic value is determined as the systolic blood pressure.

Figure 19A:
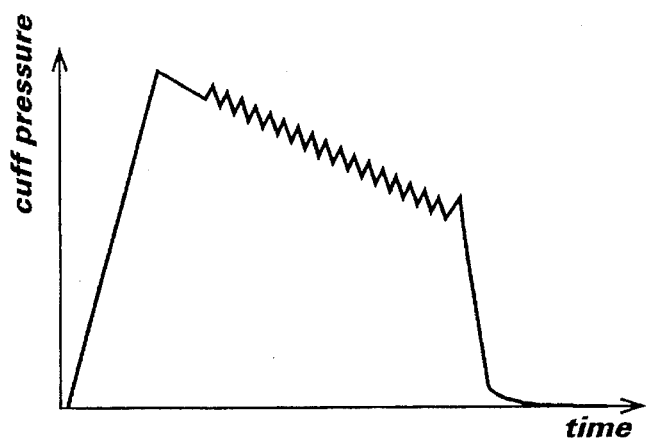
FIGS. 19A to 19D are diagrams for explaining an analysis of arterial pulses of an eleventh embodiment of the present invention.
Figure 19B:
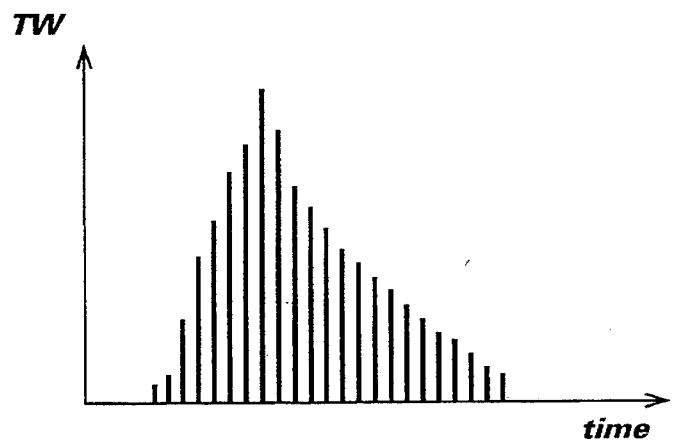
Figure 19C:
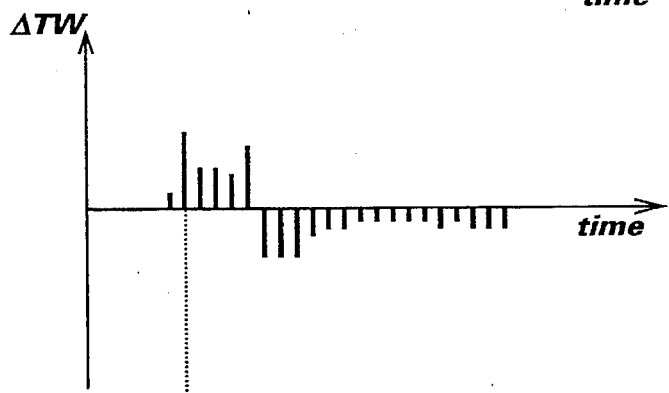
Figure 19D:
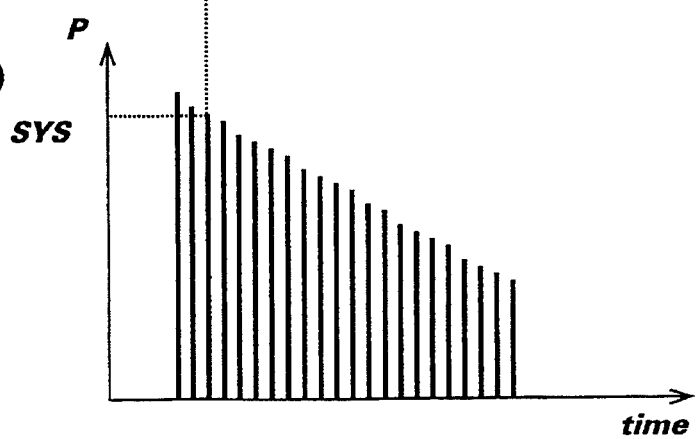

For example, when a variation of cuff pressure provided from the A/D converter 23 is shown in FIG. 19A, and a time series of the waveform values $TW_1, TW_2, \ldots$ is shown in FIG. 19B, the difference $\Delta TW$ (=TWi–TWi−1) between each of the waveform values $TW_1, TW_2, \ldots$ and the adjacent waveform value is shown in FIG. 19C. In addition, a time series of net cuff pressures $P_1, P_2, \ldots$ is shown in FIG. 19D. Therefore, the systolic blood pressure (SYS) is determined by detecting one of the net cuff pressures $P_1, P_2, \ldots$ corresponding to a maximum value of the difference $\Delta TW$. Each of the waveform values $TW_1, TW_2, \ldots$ is obtained in accordance with the procedures explained in the first or tenth embodiment. Procedures performed in this embodiment except for the above description are the substantially same as the first embodiment. By the way, though the above description is directed to the determination of the systolic blood pressure, the same technical concept can be utilized to determine a diastolic blood pressure when waveform values $TW_1, TW_2, \ldots$ having a different definition are used.

TWELFTH EMBODIMENT

In this embodiment, a ratio RT of each of waveform values $TW_1$, $TW_2$ to the adjacent waveform value ($=TW_i/TW_{i-1}$) is detected to determine a maximum value of the ratio RT. One of the waveform values $TW_1$, $TW_2$, ... corresponding to the maximum value of the ratio RT is defined as a characteristic value.

Figure 20A:
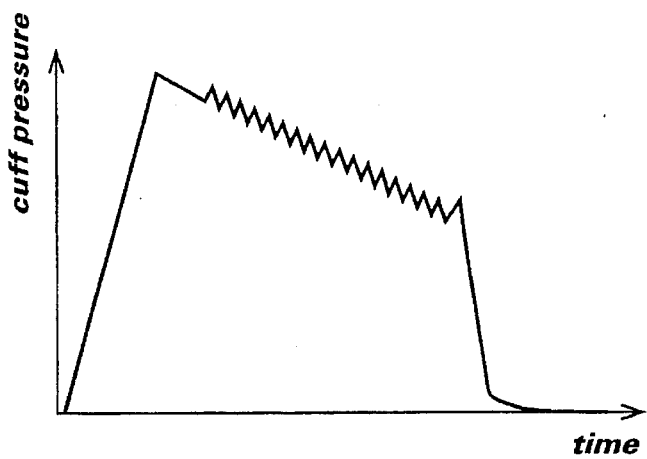
FIGS. 20A to 20D are diagrams for explaining an analysis of arterial pulses of a twelfth embodiment of the present invention.
Figure 20B:
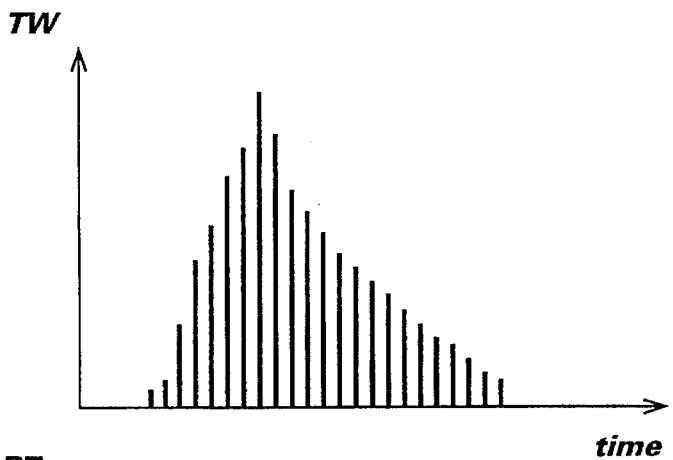
Figure 20C:
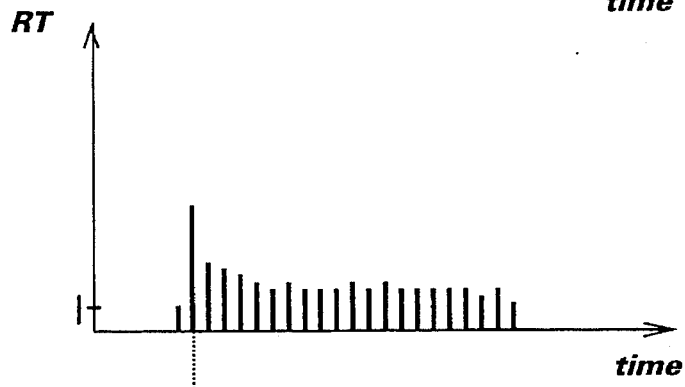
Figure 20D:
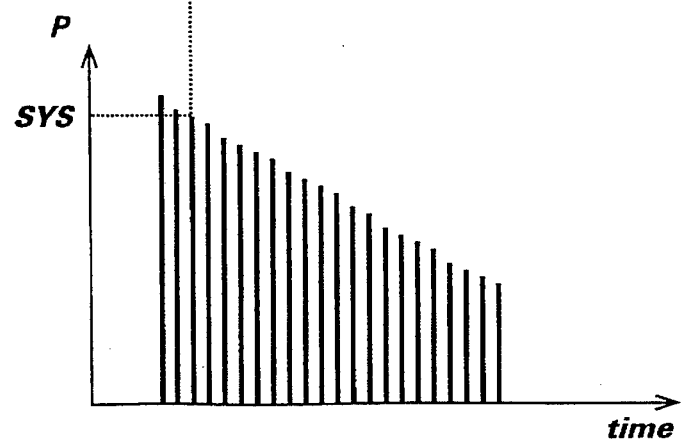

For example, when a variation of cuff pressure provided from the A/D converter 23 is shown in FIG. 20A, and a time series of the waveform values $TW_1$, $TW_2$, ... is shown in FIG. 20B, the ratio RT ($=TW_i/TW_{i-1}$) is shown in FIG. 20C. In addition, a time series of net cuff pressures $P_1$, $P_2$, ... is shown in FIG. 20D. Therefore, a systolic blood pressure (SYS) is determined by detecting one of the net cuff pressures $P_1$, $P_2$, ... corresponding to the maximum value of the ratio RT. Procedures performed in this embodiment except for the above description are the substantially same as the first embodiment. By the way, though the above description is directed to the determination of the systolic blood pressure, the same technical concept can be utilized to determine a diastolic blood pressure when waveform values $TW_1$, $TW_2$, ... having a different definition are used.

THIRTEENTH EMBODIMENT

In this embodiment, a compensational operation is performed by the blood pressure determining device 7 for more accurately determining systolic and diastolic blood pressures of a subject. Though the following explanations are directed to procedures of determining the systolic blood pressure, the same technical concept can be utilized in case of determining the diastolic blood pressure.

The blood pressure determining device 7 of this embodiment is capable of providing two provisional blood pressures for the compensational operation and determining as the systolic blood pressure a sum of compensated blood pressures which are obtained by multiplying the provisional blood pressures by predetermined weight coefficients, respectively. That is, the blood pressure determining device 7 comprises first and second blood pressure deriving sections.

A first provisional blood pressure ($SYS_1$) is determined by the first blood pressure deriving section in accordance with waveform values $TW_1$, $TW_2$, ... which are obtained by the procedures of the first or tenth embodiment. A net cuff pressure corresponding to a maximum waveform value ($TW_{max}$) of the waveform values $TW_1$, $TW_2$, ... is determined as the first provisional blood pressure ($SYS_1$). For example, as shown in FIGS. 21A and 21B, when the maximum waveform value ($TW_{max}$) is a waveform value $TW_8$ which is defined as a characteristic value, the net cuff pressure $P_8$ corresponding to the waveform value $TW_8$ is determined as the first provisional blood pressure ($SYS_1$).

Figure 22:
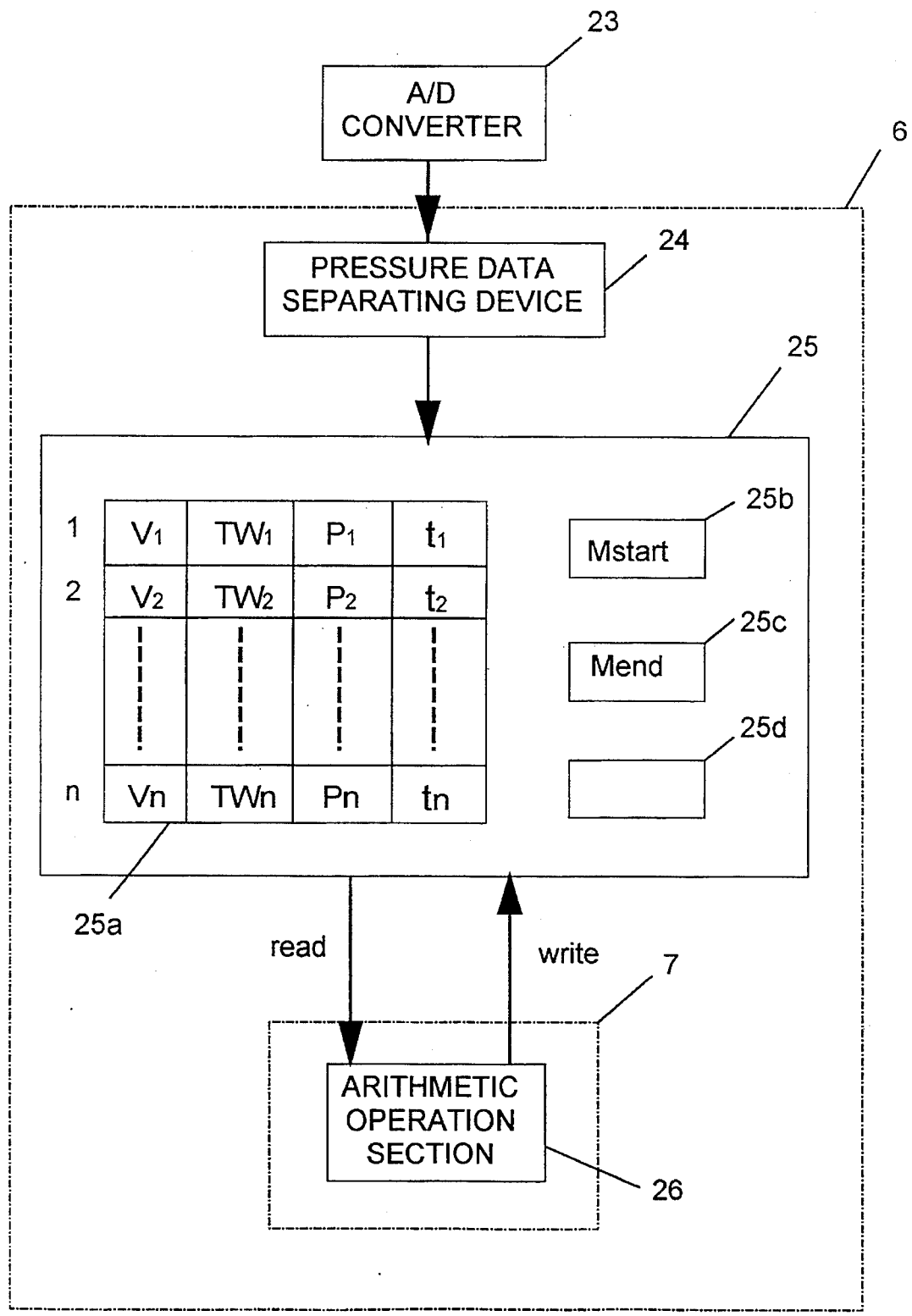
FIG. 22 is a block diagram showing an important portion of a blood pressure measuring system of the thirteenth embodiment.
Figure 23A:
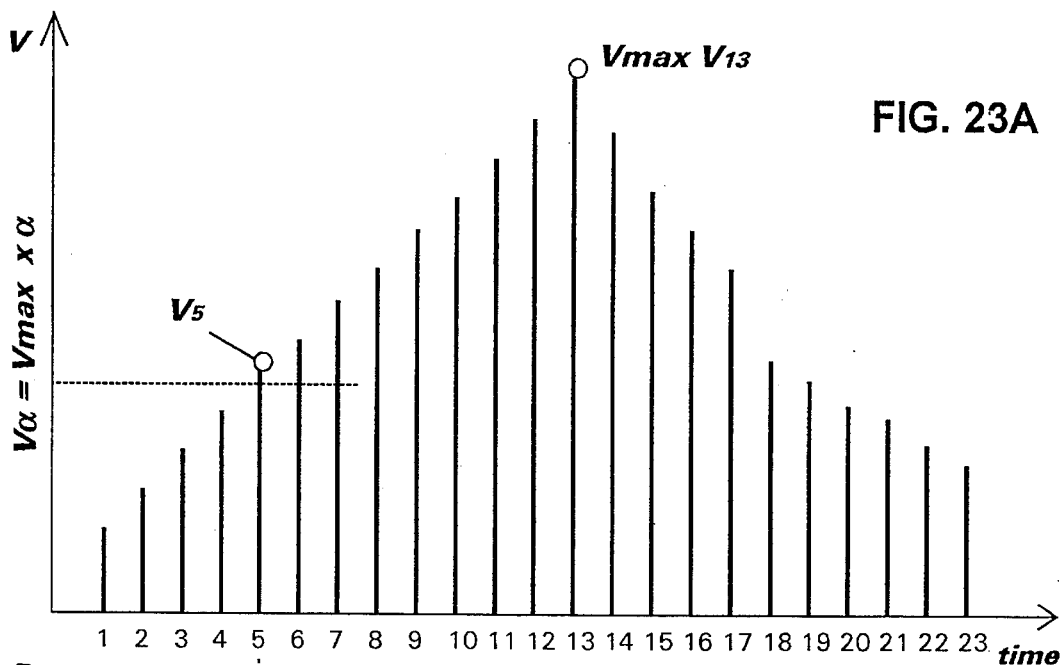
FIGS. 23A and 23B are diagrams for explaining an analysis of arterial pulses of the thirteenth embodiment.
Figure 23B:
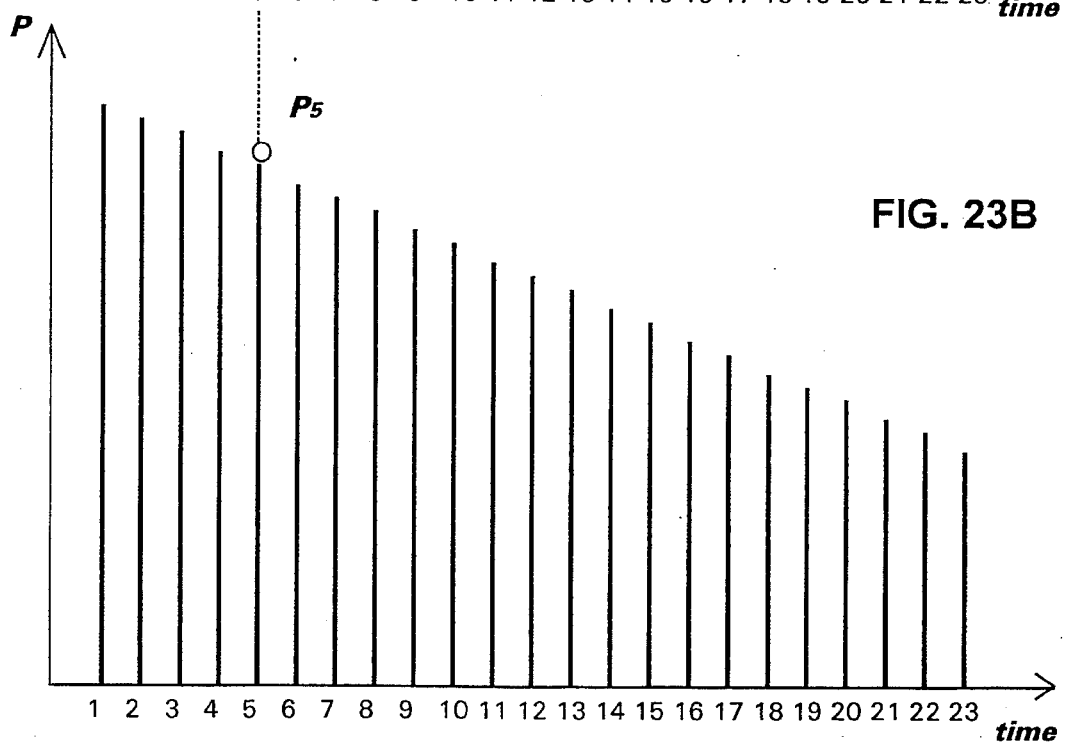

On the other hand, a second provisional blood pressure ($SYS_2$) is determined by the second blood pressure deriving section in accordance with arterial pulse values $V_1$, $V_2$, ... which are obtained by the procedures of the first or tenth embodiment. A pulse height H or area S of a waveform of an arterial pulse is used as the arterial pulse value V. For example, as shown in FIG. 22, each of the arterial pulse values $V_1$, $V_2$, ..., is stored in a data storing range 25a of the memory 25 together with the corresponding waveform value $TW_i$, net cuff pressure $P_i$ and sampling time $t_i$. In addition, as shown in FIG. 23A, a maximum arterial pulse value (Vmax $=V_{13}$) is detected, and a threshold value $V\alpha(=\alpha \times V_{max})$ is determined by multiplying the maximum arterial pulse value $V_{max}$ by a predetermined constant $\alpha$. A particular arterial pulse value ($V_5$ of FIG. 23A) which exceeds firstly the threshold value $V\alpha$ is selected from the time series of the arterial pulse values $V_1$, $V_2$, .... A net cuff pressure $P_5$ corresponding to the particular arterial pulse value $V_5$ is determined as the second provisional blood pressure ($SYS_2$), as shown in FIG. 23B.

Compensated blood pressures are obtained by multiplying the first and second provisional blood pressures $SYS_1$ and $SYS_2$ by weight coefficients $\epsilon RW$ and $\epsilon V$, respectively. A sum of the compensated blood pressures is determined as the systolic blood pressure SYS. That is, the following operation is performed, $$SYS = \epsilon TW \times SYS_1 + \epsilon V \times SYS_2$$

wherein $\epsilon TW$ and $\epsilon V$ are the weight coefficients which are determined by the use of a change ratio PERT. For example, as shown in FIGS. 21A and 21B, the change ratio PERT is defined as a ratio of a first compensated waveform value $TW_4$ to the maximum waveform value $TW_{max}$. The first compensated waveform value $TW_4$ is obtained by adding a predetermined pressure $\Delta P$ to the net cuff pressure $P_8$ corresponding to the maximum waveform value ($TW_{max}=TW_8$ of FIG. 21A) to detect a compensated pressure $P_4$, and determining a waveform value ($TW_4$) corresponding to the compensated pressure $P_4$ ($=P_8+\Delta P$). That is, the change ratio PERT is presented by the following expression, $$PERT = TW_4/TW_{max}$$

From thus obtained change ratio PERT, each of the weight coefficients $\epsilon TW$ aria $\epsilon v$ is defined as follows, when PERT<q, $\epsilon TW=0$, when $q \leq PERT \leq r$, $\epsilon TW=(r-PERT)/(r-q)$, when PERT>r, $\epsilon TW=1$, when PERT<q, $\epsilon V=1$, when $q \leq PERT \leq r$, $\epsilon V=(PERT-q)/(r-q)$, when PERT <r, $\epsilon V=0$, wherein the weight coefficients ($\epsilon TW$, $\epsilon V$) satisfy the following conditions, $0 < \epsilon TW, \epsilon V \leq 1$, and values (q, r) satisfy the following conditions, $0 < q, r < 1$.

Figure 24:
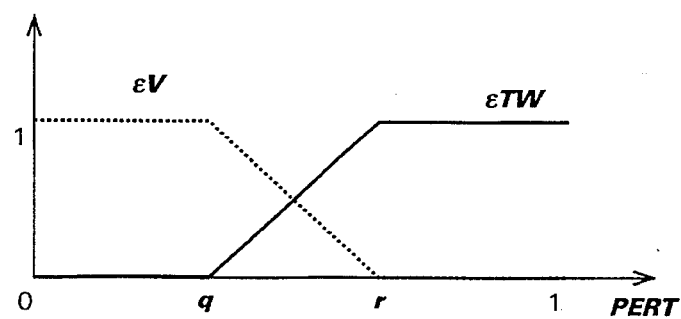
FIG. 24 is a diagram for showing a relation between weight coefficients ($\epsilon TW$, $\epsilon V$) used in the thirteenth embodiment.

Therefore, a relation between the weight coefficients $\epsilon TW$ and $\epsilon V$ is shown in FIG. 24.

When the change ratio is near 1 (PERT>r), that is, in case of a small variation of the waveform value TW, the weight coefficients $\epsilon TW$ and $\epsilon V$ are presented as follows, $\epsilon TW=1$, $\epsilon V=0$, so that $SYS=SYS_1$ is obtained. Therefore, the first provisional blood pressure $SYS_1$ derived in accordance with the waveform values is determined as the systolic blood pressure SYS.

On the other hand, when the change ratio is near 0 (PERT<q), that is, in case of a large variation of the waveform value TW, the weight coefficients $\epsilon TW$ and $\epsilon V$ are presented as follows, $\epsilon TW=0$, $\epsilon V=1$, so that $SYS=SYS_2$ is obtained. Therefore, the second provisional blood pressure $SYS_2$ derived in accordance with the arterial pulse values is determined as the systolic blood pressure SYS.

As described above, since the two provisional blood pressures $SYS_1$ and $SYS_2$ are selectively used in response to the change ratio PERT, the determination of the systolic blood pressure SYS can be more accurately performed as compared with the case of using one of the provisional blood pressures. In addition, when both provisional blood pressures $SYS_1$ and $SYS_2$ are used, that is, when $q \leq PERT \leq r$, an error in measurement of the systolic blood pressure caused by individual difference of the subject can be prevented effectively by performing a weighing to the provisional blood pressures $SYS_1$ and $SYS_2$.

By the way, in place of the above defined change ratio PERT, it is possible to use another change ratio PERT. That is, a pressure range is set around a net cuff pressure corresponding to the maximum waveform value $TW_{max}$. An average waveform value $TW_{ave}$ of the waveform values associated with the pressure range is calculated. As a result, the change ratio PERT is presented by the following expression, $$PERT = TW_{ave}/TW_{max}$$

In addition, since a cuff pressure of an inflated cuff is decreased by gradually exhausting the pressurized air of the cuff to the outside, a pressure difference of before and after one arterial pulse is almost fixed. Therefore, it is also possible to use a change ratio of a particular waveform value to the maximum waveform value $TW_{max}$ in place of the above defined change ratio. The particular waveform value is defined as a waveform value corresponding to a particular arterial pulse which precedes by a predetermined pulse count prior to an arterial pulse corresponding to the maximum waveform value $TW_{max}$. Furthermore, it is also possible to use a change ratio PERT which is defined as a ratio of a second compensated waveform value to the maximum waveform value $TW_{max}$. The second compensated waveform value is obtained by subtracting a predetermined pressure from the net cuff pressure corresponding to the maximum waveform value $TW_{max}$ to detect a compensated pressure, and determining a waveform value corresponding to the compensated pressure. Besides the above, it is possible to use a change ratio of a specific waveform value to the maximum waveform value $TW_{max}$. The specific waveform value is defined as an average of the first and second compensated waveform values.

FOURTEENTH EMBODIMENT

In this embodiment, weight coefficients $\epsilon TW$ and $\epsilon V$ are determined by the following procedures. However, a change ratio PERT is calculated in accordance with the same manner as the thirteenth embodiment. The arithmetic operation section 26 comprises data table which is composed of a read only memory (ROM) for determining the weight coefficients $\epsilon TW$ and $\epsilon V$. The contents of the data table corresponding to the weight coefficients $\epsilon TW$ and $\epsilon V$ are shown in FIG. 25A and 25B. By the data table of FIG. 25A, a predetermined value with respect to the weight coefficient $\epsilon TW$, that is, $DT(O, j, k)$, {wherein $0 \leq j \leq 4$, $0 \leq k \leq 4$}, is determined in accordance with a change ratio PERT (DTW(O)~DTW(4)) and a first provisional blood pressure $SYS_1$ (DPS(0)~DPS(4)) derived by the use of the waveform values. On the other hand, by the data table of FIG. 25B, a predetermined value with respect to the weight coefficient $\epsilon V$, that is, $DT(1, j, k)$, {wherein $0 \leq j \leq 4$, $0 \leq k \leq 4$}, is determined in accordance with the change ratio PERT (DTW(0)~DTW(4)) and the first provisional blood pressure $SYS_1$ (DPS(0)~DPS(4)).

That is, on both data tables, membership functions $DT(0, j, k)$ and $DT(1, j, k)$ are set for determining the weight coefficients $\epsilon TW$ and $\epsilon V$ in accordance with the change ratio PERT and the first provisional blood pressure $SYS_1$.

Figure 26:
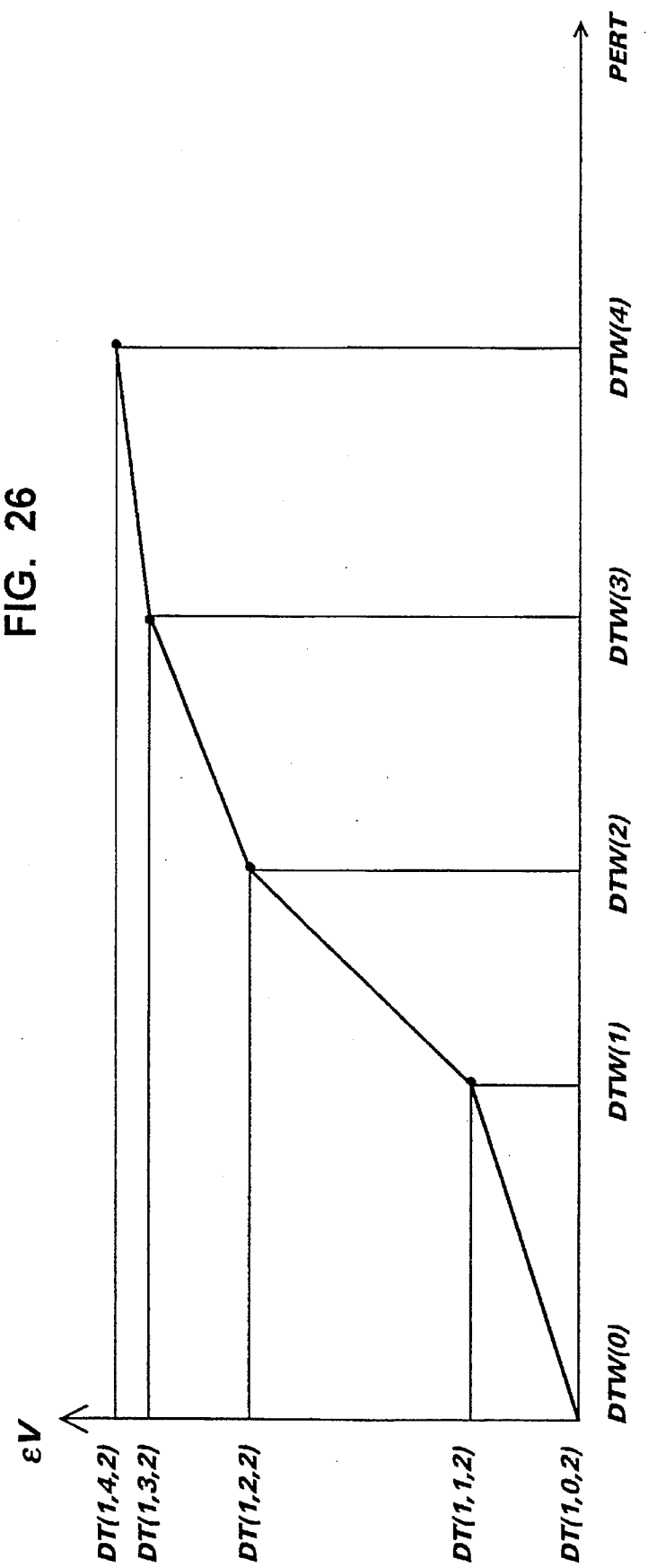
FIG. 26 is a diagram showing a relation between the weight coefficient $\epsilon V$ and a change ratio PERT of the fourteenth embodiment.

Next, a method of determining the weight coefficients $\epsilon TW$ and $\epsilon V$ by the use of the above membership functions $DT(0, j, k)$ and $DT(1, j, k)$ is explained below. Referring to the data tables with respect to the change ratio PERT obtained by the procedures of the thirteenth embodiment, a value $I_T$ satisfying the following relation, that is, $DTW(I_T) < PERT < DTW(I_T+1)$ is determined. Subsequently, referring to the data tables with respect to the first provisional blood pressure $SYS_1$ derived from waveform values, a value Is satisfying the following relation, that is, $DPS(I_s) < SYS_1 < DPS(I_s+1)$ is determined. The weight coefficients $\epsilon TW$ and $\epsilon V$ are respectively determined by substituting the values $I_T$ and $I_s$ into the following expressions, $\epsilon TW = \{DT(0, I_T, I_S) \times (DTW(I_T+1)-PERT) \times (DPS(I_s+1)-SYS_1) + DT(O, I_T+1, I_S) \times (PERT-DTW(I_T)) \times (DPS(I_s+1)-SYS_1) + DT(0, I_T, I_s+1) \times (DTW(I_T+1)-PERT) \times (SYS_1-DPS(I_s)) + DT(0, I_T+1, Is+1) \times (PERT-DTW(I_T)) \times (SYS_1-DPS(I_s))\}/\{(DTW(I_T+1)-DTW(I_T)) \times (DPS(I_s+1)-DPS(I_s))\}$ $\epsilon V = \{DT(1, I_T, I_S) \times (DTW(I_T+1)-PERT) \times (DPS(I_s+1)-SYS1) + DT(1, I_T+1, I_s) \times (PERT-DTW(I_T)) \times (DPS(I_s+1)-SYS_1) + DT(1, I_T, I_s+1) \times (DTW(I_T+1)-PERT) \times (SYS_1-DPS(I_s)) + DT(1, I_T+1, I_s+1) \times (PERT-DTW(I_T)) \times (SYS_1-DPS(I_s))\}/\{(DTW(I_T+1)-DTW(I_T)) \times (DPS(I_s+1)-DPS(I_s))\}$ When the first provisional blood pressure $SYS_1$ is equal to DPS(2), that is, $SYS_1 = DPS(2)$, the weight coefficient $\epsilon V$ is varied in response to the change ratio PERT, as shown in FIG. 26. The weight coefficient $\epsilon V$ is also varied in response to the first provisional blood pressure $SYS_1$.

Therefore, a systolic blood pressure can be accurately determined by compensating the first provisional blood pressure $SYS_1$ with the above determined weight coefficients $\epsilon TW$ and $\epsilon V$. In addition, though the membership functions are set with respect to the first provisional blood pressure and the change ratio in the above explanation, it is also possible to set membership functions with respect to an arterial pulse value and the change ratio.

I claim:

1. A blood pressure measuring system comprising:

an occluding cuff adapted in use to be attached to a selected portion of a subject;

pressurizing means for providing an occluding pressure of said cuff;

pressure bleeding means for gradually decreasing said occluding pressure;

a pressure sensor for sensing an instantaneous cuff pressure measurement and providing an electrical signal indicative thereof;

pressure data separating means for separating from said electrical signal an arterial pulse component superimposed on a net cuff pressure during a pressure bleeding period of gradually decreasing said occluding pressure so as to separately extract said arterial pulse component and said net cuff pressure;

blood pressure determining means for determining systolic and diastolic blood pressures in accordance with said net cuff pressure and said arterial pulse component provided from said pressure data separating means; and display means for displaying the respective systolic and diastolic blood pressures;

said pressure data separating means including a waveform analyzing means for determining a waveform value of each arterial pulse by the use of pulse width and pulse height of said arterial pulse;

said blood pressure determining means including a characteristic value detecting section detecting a characteristic value from a time series of said waveform values and including a blood pressure deriving section for deriving said systolic and diastolic blood pressures in accordance with said net cuff pressure corresponding to said characteristic value.

2. A blood pressure measuring system as set forth in claim 1, wherein said waveform analyzing means provides said waveform value which is a ratio of a pulse height to a pulse width of each arterial pulse.

3. A blood pressure measuring system as set forth in claim 1, wherein said-waveform analyzing means provides said waveform value which is a ratio of a pulse height to the square of a pulse width of each arterial pulse.

4. A blood pressure measuring system as set forth in claim 1, wherein said waveform analyzing means provides, for each arterial pulse, said waveform value which is one of a pre-peak duration and a post-peak duration, said pre-peak and post-peak durations being defined within a pulse width of said arterial pulse immediately before and after a point of peak pulse height, respectively.

5. A blood pressure measuring system as set forth in claim 1, wherein said waveform analyzing means provides, for each arterial pulse, said waveform value which is a ratio of a pre-peak duration to a post-peak duration, said pre-peak and post-peak durations being defined within a pulse width of said arterial pulse immediately before and after a point of peak pulse height, respectively.

6. A blood pressure measuring system as set forth in claim 1, wherein said waveform analyzing means provides, for each arterial pulse, said waveform value which is a ratio of one of a pre-peak duration and a post-peak duration to an overall pulse width of said arterial pulse, said pre-peak and post-peak durations being defined within a pulse width of said arterial pulse immediately before and after a point of peak pulse height, respectively.

7. A blood pressure measuring system as set forth in claim 1, wherein said waveform analyzing means provides, for each arterial pulse, as said waveform value which is an integral of said arterial pulse for one of a pre-peak duration and a post-peak duration, said pre-peak and post-peak durations being defined within a pulse width of said arterial pulse immediately before and after a point of peak pulse height, respectively.

8. A blood pressure measuring system as set forth in claim 1, wherein said waveform analyzing means provides, for each arterial pulse, said waveform value which is a ratio of a fore-area to a rear-area, said fore-area and rear-area being integrals of said arterial pulse respectively for a pre-peak duration and a post-peak duration, said pre-peak and post-peak durations being defined within a pulse width of said arterial pulse immediately before and after a point of peak pulse height, respectively.

9. A blood pressure measuring system as set forth in claim 1, wherein said waveform analyzing means provides, for each arterial pulse, said waveform value which is a ratio of one of a fore-area and a rear-area to an overall area which is an integral of each arterial pulse for a duration of its pulse width, said fore-area and rear-area being integrals of said arterial pulse respectively for a pre-peak duration and a post-peak duration, said pre-peak and post-peak durations being defined within a pulse width of said arterial pulse immediately before and after a point of peak pulse height, respectively.

10. A blood pressure measuring system as set forth in claim 1, wherein said characteristic value is defined to be a maximum of said waveform value.

11. A blood pressure measuring system as set forth in claim 1, wherein said characteristic value is defined to be a particular one of said waveform values, said particular waveform value being selected such that a difference between said particular waveform value and a waveform value of the previous arterial pulse is maximum.

12. A blood pressure measuring system as set forth in claim 1, wherein said characteristic value is defined to be a particular one of said waveform values, said particular waveform value being selected such that a ratio of said particular waveform value to a waveform value of the previous arterial pulse is maximum.

13. A blood pressure measuring system as set forth in claim 1, wherein said pressure data separating means includes an arterial pulse deriving means for providing, for each arterial pulse, an arterial pulse value which is a pulse height or integral of said arterial pulse with respect to time, and wherein said blood pressure determining means comprises a first blood pressure deriving section for deriving first systolic and diastolic blood pressures based upon said waveform values and a second blood pressure deriving section for deriving second systolic and diastolic blood pressures based upon said arterial pulse values, and a blood pressure compensation section for determining said systolic and diastolic blood pressure based upon said first and second systolic and diastolic blood pressures.

14. A blood pressure measuring system as set forth in claim 13, wherein said blood pressure compensation section provides a change ratio of a specific one of said waveform values to said characteristic value, said specific waveform value being selected to have a predetermined relation to said characteristic value, said blood pressure compensation section determining, based upon said change ratio, said systolic blood pressure which is one of said first and second systolic blood pressures or a combined pressure of said first and second systolic blood pressures.

15. A blood pressure measuring system as set forth in claim 14, wherein said specific waveform value is defined to correspond to a high net cuff pressure which is higher by a predetermined extent than said net cuff pressure associated with said characteristic value.

16. A blood pressure measuring system as set forth in claim 14, wherein said specific waveform value is defined to correspond to a low net cuff pressure which is lower by a predetermined extent than said net cuff pressure associated with said characteristic value.

17. A blood pressure measuring system as set forth in claim 14, wherein said specific waveform value is defined to correspond to an average net cuff pressure of high and low net cuff pressures which are respectively higher and lower by a predetermined extent than said net cuff pressure associated with said characteristic value.

18. A blood pressure measuring system as set forth in claim 14, wherein said set of combined pressures are defined to be a sum of the product of said first systolic blood pressure times a weight coefficient and the product of said second systolic blood pressure times a weight coefficient, said weight coefficients being selected for said first and second systolic blood pressures in correspondence to said change ratio.

19. A blood pressure measuring system as set forth in claim 18, wherein said weight coefficient is a weighted average of said first and second systolic blood pressures with the use of a membership function having said change ratio as a parameter.

20. A blood pressure measuring system as set forth in claim 18, wherein said weight coefficient is a weighted average of said first and second systolic blood pressures with the use of a membership function having said change ratio and said first and second systolic blood pressures as parameters.

21. A blood pressure measuring system as set forth in claim 18, wherein said weight coefficient is a weighted average of said first and second systolic blood pressures with the use of a membership function having said change ratio and said net cuff pressure as parameters.

* * * * *